(12) United States Patent
Weinberger et al.

(10) Patent No.: US 12,013,400 B2
(45) Date of Patent: Jun. 18, 2024

(54) RADICAL DOSIMETRY METHODS FOR IN VIVO HYDROXYL RADICAL PROTEIN FOOT-PRINTING

(71) Applicant: GenNext Technologies, Inc., Montara, CA (US)

(72) Inventors: Scot Randy Weinberger, Montara, CA (US); Ronald Carl Orlando, Athens, GA (US); Joshua Shane Sharp, Oxford, MS (US); Robert Wallace Egan, Reno, NV (US); Jeffrey Jonathan Persoff, San Jose, CA (US)

(73) Assignee: GENNEXT TECHNOLOGIES, INC., Half Moon Bay, CA (US)

( * ) Notice: Subject to any disclaimer, the term of this patent is extended or adjusted under 35 U.S.C. 154(b) by 764 days.

(21) Appl. No.: 17/168,472

(22) Filed: Feb. 5, 2021

(65) Prior Publication Data

US 2021/0156869 A1    May 27, 2021

Related U.S. Application Data

(63) Continuation-in-part of application No. PCT/US2020/012430, filed on Jan. 6, 2020, which is
(Continued)

(51) Int. Cl.
*G01N 33/68*    (2006.01)
*C23C 18/14*    (2006.01)
(Continued)

(52) U.S. Cl.
CPC ......... *G01N 33/6803* (2013.01); *C23C 18/14* (2013.01); *G01N 21/59* (2013.01);
(Continued)

(58) Field of Classification Search
CPC ...... C23C 18/14; G01N 21/59; G01N 21/631; G01N 21/6428; G01N 33/6803; G01N 2021/6439; H01J 49/0036
See application file for complete search history.

(56) References Cited

U.S. PATENT DOCUMENTS 2,987,456 A    6/1961 Lauer
3,354,315 A    11/1967 Preston et al.
(Continued)

FOREIGN PATENT DOCUMENTS

EP    0347039 A3    12/1989
GB    2358244 A    7/2001
(Continued)

OTHER PUBLICATIONS

Zhang, H., et al., Fast photochemical oxidation of proteins for comparing structures of protein-ligand complexes: the calmodulin-peptide model system. Anal Chem, 2011. 83(1): p. 311-8.
(Continued)

*Primary Examiner* — Mark R Gaworecki
(74) *Attorney, Agent, or Firm* — Rimon Law, P.C.

(57) ABSTRACT

Flash Photo-Oxidation Device and Higher Order Structural Analysis is employed for higher order structural analysis of biomolecules. Biomolecular higher order structure (HOS) results from the confounded superimposition of a biomolecule's secondary, tertiary, and quaternary structure and defines the manner in which a biomolecule presents itself and interacts with other biomolecules in living systems. A rapidly growing class of therapeutic drugs, known as biotherapeutics, comprises a variety of proteins, whose therapeutic properties are inherently linked and dependent upon their HOS. As such, HOS analysis of biotherapeutics is an important analytical requirement in the biopharmaceutical industry. The present invention provides new means and methods for the determination of biopharmaceutical HOS
(Continued)

and associated conformation using improved devices and methodologies for flash photo-oxidation of proteins to determine their higher order biomolecular structure, and such is responsive to the increased demand for new and improved HOS analytical means in the biopharmaceutical industry.

19 Claims, 24 Drawing Sheets

Related U.S. Application Data a continuation-in-part of application No. 16/316,006, filed on Jan. 7, 2019, now Pat. No. 10,816,468, application No. 17/168,472, filed on Feb. 5, 2021 is a continuation-in-part of application No. PCT/US2019/057059, filed on Oct. 18, 2019, which is a continuation-in-part of application No. 16/316,006, filed as application No. PCT/US2018/034682 on May 25, 2018, now Pat. No. 10,816,468.

(60) Provisional application No. 62/788,219, filed on Jan. 4, 2019, provisional application No. 62/747,247, filed on Oct. 18, 2018, provisional application No. 62/511,571, filed on May 26, 2017, provisional application No. 63/128,439, filed on Dec. 21, 2020.

(51) Int. Cl.
*G01N 21/59* (2006.01)
*G01N 21/63* (2006.01)
*G01N 21/64* (2006.01)
*H01J 49/00* (2006.01)

(52) U.S. Cl.
CPC ....... *G01N 21/631* (2013.01); *G01N 21/6428* (2013.01); *H01J 49/0036* (2013.01); *G01N 2021/6439* (2013.01)

(56) References Cited

U.S. PATENT DOCUMENTS

| | | | |
|---|---|---|---|
| 4,000,973 | A | 1/1977 | Petersen |
| 5,021,646 | A | 6/1991 | Weinberger et al. |
| 5,037,100 | A | 8/1991 | Hlousek |
| 5,037,523 | A | 8/1991 | Weinberger et al. |
| 5,443,791 | A | 8/1995 | Cathcart et al. |
| 5,602,446 | A | 2/1997 | Kolber et al. |
| 5,807,750 | A | 9/1998 | Baum et al. |
| 5,936,728 | A | 8/1999 | Bouzid |
| 6,254,689 | B1 | 7/2001 | Meder |
| 6,741,347 | B1 | 5/2004 | Scaiano et al. |
| 7,812,311 | B2 | 10/2010 | DeCamp et al. |
| 7,817,270 | B2 | 10/2010 | Gusev |
| 8,446,587 | B2 | 5/2013 | Gusev |
| 9,279,814 | B2 | 3/2016 | Brenowitz et al. |
| 10,851,335 | B2 | 12/2020 | Jones et al. |
| 2002/0033369 | A1 | 3/2002 | Bender |
| 2003/0036206 | A1 | 2/2003 | Chien et al. |
| 2003/0074062 | A1 | 3/2003 | Monzyk |
| 2004/0241872 | A1 | 12/2004 | Wegrzyn et al. |
| 2005/0218082 | A1 | 10/2005 | Williamson et al. |
| 2005/0266065 | A1 | 12/2005 | Perrier et al. |
| 2006/0257877 | A1 | 11/2006 | Anderle |
| 2007/0152154 | A1 | 7/2007 | DeCamp et al. |
| 2008/0165363 | A1 | 7/2008 | Gusev |
| 2009/0074611 | A1 | 3/2009 | Monzyk et al. |
| 2010/0081159 | A1 | 4/2010 | Ledebeva et al. |
| 2010/0137163 | A1 | 6/2010 | Link et al. |
| 2013/0119277 | A1 | 5/2013 | Atzler et al. |
| 2014/0030751 | A1* | 1/2014 | Sharp ................ G01N 33/6848 435/23 |
| 2018/0079998 | A1 | 3/2018 | Jones et al. |

FOREIGN PATENT DOCUMENTS

| | | |
|---|---|---|
| JP | 2009192259 A | 8/2009 |
| WO | 2016/130553 A1 | 8/2016 |
| WO | 2016/164244 A1 | 10/2016 |
| WO | 2018/218163 A1 | 11/2018 |
| WO | 2020/142785 A1 | 7/2020 |
| WO | 2020/146425 A1 | 7/2020 |

OTHER PUBLICATIONS

Johnson, D.T., L.H. Di Stefano, and L.M. Jones, Fast photochemical oxidation of proteins(FPOP): A powerful mass spectrometry based structural proteomics tool. J Biol Chem, 2019.
Espino, J.A. and L.M. Jones, Illuminating Biological Interactions with in Vivo Protein Footprinting. Anal Chem, 2019. 91(10): p. 6577-6584.
Chea E.E. and L.M. Jones, Modifications generated by fast photochemical oxidation of proteins reflect the native conformations of proteins. Protein Sci, 2018. 27(6): p. 1047-1056.
Chea, E.E. and L.M. Jones, Analyzing the structure of macromolecules in their native cellular environment using hydroxyl radical footprinting. Analyst, 2018. 143(4): p. 798-807.
Aprahamian, M.L., et al., Rosetta Protein Structure Prediction from Hydroxyl Radical Protein Footprinting Mass Spectrometry Data. Anal Chem, 2018. 90(12): p. 7721-7729.
Rinas, A., et al., Development of a Microflow System for In-Cell Footprinting Coupled with Mass Spectrometry. Anal Chem, 2016. 88(20): p. 10052-10058.
Rinas, A., J.A. Espino, and L.M. Jones, An efficient quantitation strategy for hydroxyl radical-mediated protein footprinting using Proteome Discoverer. Anal Bioanal Chem, 2016. 408(11): p. 3021-31.
Rinas, A. and L.M. Jones, Fast photochemical oxidation of proteins coupled to multidimensional protein identification technology (MudPIT): expanding footprinting strategies to complex systems. J Am Soc Mass Spectrom, 2015. 26(4): p. 540-6.
Espino, J.A., V.S. Mali, and L.M. Jones, In Cell Footprinting Coupled with Mass Spectrometry for the Structural Analysis of Proteins in Live Cells. Anal Chem, 2015. 87(15): p. 7971-7978.
Jones, L.M., et al., Fast photochemical oxidation of proteins for epitope mapping. Anal Chem, 2011. 83(20): p. 7657-61.
Poor, T.A., et al., Probing the paramyxovirus fusion (F) protein-refolding event from pre- to postfusion by oxidative footprinting. Proc Natl Acad Sci U S A, 2014. 111(25): p. E2596-605.
Jones, L.M., et al., Complementary MS methods assist conformational characterization of antibodies with altered S-S bonding networks. J Am Soc Mass Spectrom, 2013. 24(6): p. 835-45.
Cong, M. et al., Research on A Novel R-0 Wafer Handling Robot, Aug. 2007, 2007 IEEE International Conference on Automation and Logistics, pp. 597-602 (Year: 2007).
Sharp, et al. Real Time Normalization of Fast Photochemical Oxidation of Proteins Experiments by Inline Adenine Radical Dosimetry, Analytical Chemistry, vol. 90, pp. 12625-12630, Oct. 5, 2018.
Roush, et al., Intrinsic Buffer Hydroxyl Radical Dosimetry Using Tris(Hydroxymethyl)Aminomethane, bioRxiv, pp. 1-6, Oct. 19, 2019.
PCT/US2019/057059, International Search Report and Written Opinion, mailed Dec. 31, 2019.
PCT/US2020/012430, International Search Report and Written Opinion, mailed Mar. 12, 2020.
EP 18805903.4, Extended European Search Report, mailed Jan. 29, 2021.
EP 18805903.4, Response to Extended European Search Report, mailed Jan. 29, 2021, filed Jun. 9, 2021.
EP 18805903.4, First Examination Report, mailed Oct. 21, 2021.
EP 18805903.4, Response to First Examination Report, mailed Oct. 21, 2021, filed Jan. 26, 2022.
EP 23172498.0, Extended European Search Report, mailed Jul. 3, 2023.

(56) References Cited

OTHER PUBLICATIONS

EP 18805903.4, Response to Extended European Search Report, mailed Jan. 29, 2021, filed Sep. 25, 2023.
EP 20735970.4, Extended European Search Report, mailed Sep. 9, 2022.
EP 20735970.4, Response to Extended European Search Report, mailed Sep. 9, 2022, filed Mar. 27, 2023.
Jp2021-539578, Office Action, mailed Oct. 31, 2023 plus translation.
PCT/US2021/060394, International Search Report and Written Opinion, mailed Mar. 24, 2022.
Xu et al., "Hydroxyl radical-mediated modification of proteins as probes for structural proteomics", Chemical Reviews, 2007, vol. 107, No. 8, pp. 3514-3543.
Takamoto et al., "Radiolytic protein footprinting with mass spectrometry to probe the structure of macromolecular complexes", Annu. Rev. Biophys. Biomol Struct. 2006, 35:251-76.
Niu et al., "Dosimetry determines the inital OH radical concentration in fast photochemical oxidation of proteins (FPOP)", J. Am. Soc. Mass Spectrom. (2015) 26:843-846.
U.S. Appl. No. 13/951,708, Final Rejection dated Feb. 10, 2015.
Gau et al., "Fast photochemical oxidation of protein footprints faster than protein unfolding", Anal. Chem. 2009, 81, 6563-6571.
U.S. Appl. No. 11/970,676, Non-final Office Action dated Apr. 1, 2009.
Hambly et al. Laser flash photolysis of hydrogen peroxide to oxidize protein solvent-accessible residues on the microsecond timescale:, J Am Soc Mass Spectrom 2005, 16, 2057-2063.
Scaiano, Dr. J.C., "Laser Flash Photolysis: From Lindqvist to Luzchem", technical report No. 001, Luzchem Research, Inc., Ottawa, Canada, Aug. 2003.
Vahidi, et al., "Probing the time scale of FPOP (fast photochemical oxidation of proteins): radical reactions extend over tens of milliseconds", J. Am. Soc. Mass Spectrom. (2016) 27:1156-1164.
Li, et al., "High Structural Resolution Hydroxyl Radical Protein Footprinting Reveals an Extended Robo1-Heparin Binding Interface" JBC Papers in Press. Published on Mar. 9, 2015 as Manuscript M115.648410.
Wang, et al. "Oligomeric Structure of the Chemokine CCL5/RANTES from NMR, MS, and SAXS Data", Structure 19, 1138-1148, Aug. 10, 2011.
Li, et al., "Structural analysis of the glycosylated intact HIV-1 gp120-b12 antibody complex using hydroxyl radical protein footprinting", Biochemistry 2017, 56, 957-970.
Watson, et al., "Conformational analysis of therapeutic proteins by hydroxyl radical protein footprinting", the AAPS Journal, vol. 14, No. 2, Jun. 2012.
Xie, et al., "Hydroxyl radical dosimetry for high flux hydroxyl radical protein footprinting applications using a simple optical detection method", Anal. Chem. 2015, 87, 10719-10723.
Sharp, et al., "Analysis of protein solvent accessible surfaces by photochemical oxidation and mass spectrometry", Anal. Chem. 2004 76, 672-683.
Huang, et al., "An approach for separation and complete structural sequencing of Heparin/Heparin sulfate-like Oligosaccharides", 2013 Anal. Chem. 85 5787-5795.
Li, et al. "Improved identification and relative quantification of sites of peptide and protein oxidation for hydroxyl radical footprinting", 2013 J. Am Soc. Mass Spectrom.24 1767-1776.
Wang, et al., "Chemokine oligomerization in cell signaling and migration", Prog. Mol. Bioil. Transf. Sci. 117: 531-578, 2013.
Saladino, et al., "Aliphatic Peptidyl Hydroperoides as a source of secondary oxidation in hydroxyl radical protein footprinting", 2009 J. Am Soc. Mass Spectrom.20 1123-1126.
Watson, et al., Pulsed electron beam water radiolysis for submicrosecond hydroxyl radical protein footprinting:, 2009 Anal. Chem. 81, 2496-2505.
Bern, et al., "Conversion of methionine into homocysteic acid in heavily oxidized proteomics samples", Rapid. Commun. Mass Spectrom, 2010, 24, 768-772.
Charvatova, et al., "Quantifying protein interface footprinting by hydroxyl radical oxidation and molecular dynamics simulation: application to galectin-1", J. Am. Soc. Mass Spectrom, 2008, 19: 1692-1705.
Smedley, et al., "Probing the pH-dependent prepore to pore transition of bacillus anthracis protective antigen with differential oxidative protein footprinting", Biochemistry 2008, 47, 10694-10704.
U.S. Appl. No. 13/951,708, SB08 Form Filed Oct. 21, 2014.
JP2021-539578, Argument and Amendment filed in response to Office Action, mailed Oct. 31, 2023, filed Mar. 12, 2024, plus translation.

\* cited by examiner

RADICAL DOSIMETRY METHODS FOR IN VIVO HYDROXYL RADICAL PROTEIN FOOT-PRINTING

CROSS REFERENCE TO RELATED APPLICATIONS

This application is a Continuation-in-Part of US PCT Application Ser. No. PCT/US19/57059 filed Oct. 18, 2019; PCT/US19/57059 in turn claims priority to Ser. No. 16/316,006 filed Jan. 7, 2019, 62/788,219 filed Jan. 4, 2019, and 62/747,247 filed Oct. 18, 2018;
  Ser. No. 16/316,006 in turn claims priority to PCT/US18/34682 filed May 25, 2018 and 62/511,571 filed May 26, 2017;
this application is a Continuation-in-Part of US PCT Application Ser. No. PCT/US20/12430 filed on Jan. 6, 2020;
  PCT/US20/12430 in turn claims priority to 62/788,219 filed Jan. 4, 2019; and this application claims priority to U.S. provisional patent application Ser. No. 63/128,439 filed Dec. 21, 2020. The disclosures of all the above patents and patent applications are hereby incorporated herein by reference.

BACKGROUND

Field of the Invention

The present invention relates to a device or devices and methodologies for higher order structural analysis of biomolecules. More specifically, the present invention relates to the determination of biopharmaceutical tertiary and quaternary structure and associated conformation using improved devices and methodologies for flash photo-oxidation of proteins to determine their higher order biomolecular structure.

Related Art

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

During the last thirty years, the popularity and use of biopharmaceuticals has prospered, fostering substantial growth in the biopharmaceutical industry. This growth was fueled by the introduction of key recombinant drugs with efficacy in combating metabolic, rheumatoid-arthritic, auto-immune, and neoplastic disease. While effective, bio-therapeutics are expensive and exert substantial financial pressure upon patients and healthcare delivery. Biosimilars are therapeutics similar to but not identical to existing innovator or reference products. Unlike the case for small molecule drugs, biosimilars are not merely generic versions of original products. Conventional generics are considered to be therapeutically and molecularly equivalent to their originators. This is not the case with biosimilars, which are complex, three-dimensional biomolecules, whose heterogeneity and dependence upon production in living cells makes them quite different from classical drugs. The structures and functional activities of bio-therapeutics are exquisitely sensitive to their environments. The intended structure of a therapeutic is maintained by a delicate balance of factors, including concentration of the protein, control of post-translational modifications, pH as well as co-solutes in the formulation, and production/purification schemes. As such, biopharmaceutical structure must typically be prudently maintained, for if not held in check, undesirable and adverse pharmacological consequences can arise.

Flash lamp sources have been used to initiate photochemical reactions for a variety of chemical and biochemical species. As developed by Porter and Norrish in the late 1940's, flash photolysis has been broadly used since the mid twentieth century. In U.S. Pat. No. 2,987,456, Lauer describes a Xe flash lamp photolysis unit that catalyzes the conversion of $H_2S$ gas to free sulfur and $CS_2$, for the purpose of in-line removal of $H_2S$ gas from gas refinery exhaust.

SUMMARY

Various embodiments of present invention includes systems and methodologies that addresses various shortcomings of prior art Fast Photochemical Oxidation of Proteins (FPOP) Hydroxyl Radical Protein Foot-printing HRPF analysis by: eliminating the use of expensive and hazardous lasers; providing the means to measure and adjust for unwanted background scavenging; circumventing the requisite use of $H_2O_2$; and by providing computational algorithms and methodologies that compensate for background scavenging in a post-analytical manner.

Teachings of the prior art fail to address the specific requirements for FPOP HRPF analysis. In order to adequately support cost-effective, simplified, and safe FPOP HRPF analysis, a photo-catalytic light source, or flash photolysis system, optionally have the following features: spectral irradiance of at least 3 $mJ/mm^2$-nm (200-280 nm) to catalyze OH radical production from $H_2O_2$; pulse width less than 10 microseconds in duration (full width at half magnitude: FWHM) to prohibit artefactual change in protein HOS; and provide the means to adjust spectral irradiance in accordance with required effective OH radical concentration to improve oxidative profile reproducibility and enable comparative studies. As such, various embodiments for FPOP HRPF analysis include systems and methodology to perform radical dosimetry, in real-time, to assess and correct for trial-to-trial variation of background scavenging during the sample photo-oxidation process. Further, various embodiments of FPOP HRPF analysis does not rely upon the use of $H_2O_2$ is desired.

Various embodiments of the present invention are directed to systems and methods for the analysis of protein higher order structure comprising improved embodiments to perform flash photo-oxidation of proteins enabling advanced hydroxyl radical protein foot-printing. In some embodiments this invention provides a flash photolysis system with integrated radical dosimetry system wherein closed-loop control is established between the flash photolysis system and dosimeter to control irradiance of the flash photolysis system in response to measured changes in absorbance of a dosimeter internal standard reagent used in the measurement of effective hydroxyl radical photo-catalytic yield. In some embodiments, the device further comprises a flash photolysis system that makes use of imaging optics to transmit flash lamp light to a photolysis cell of said system. In some embodiments, the device further comprises a flash photolysis system that makes use of collection optics to transmit flash lamp light to a photolysis cell of said system. In some embodiments, the device further comprises a flash photolysis system that makes use of non-imaging optics to transmit flash lamp light to a photolysis cell of said system. In some embodiments, the photolysis cell comprises an optically transparent capillary comprised of fused silica. In some embodiments, the photolysis cell comprises an optically transparent capillary comprised of glass. In some embodiments, the photolysis cell comprises an optically transparent opto-fluidic chip comprised of quartz. In some embodiments, the photolysis cell comprises an optically transparent opto-fluidic chip comprised of glass. In some embodiments, the photolysis cell comprises a capillary that is a fluid core waveguide. In some embodiments, the photolysis cell comprises an opto-fluidic chip that serves as a fluid core waveguide. In some embodiments, the photolysis cell comprises evanescent field waveguide. In some embodiments, the photolysis cell comprises a micro-structure resonator. In some embodiments, at least one optical surface of the photolysis cell is coated with a metal oxide photo-catalyst that catalyzes the formation of OH radicals from water. In some embodiments, the photolysis cell is comprised of a sample reservoir with coated on at least one fluid contacting surface with a metal oxide photo-catalyst that catalyzes the formation of OH radicals from water. In some embodiments, the photolysis cell is comprised of a microplate coated on at least one fluid contacting surface with a metal oxide photo-catalyst that catalyzes the formation of OH radicals from water.

Various embodiments of the invention comprise a flash photolysis system with integrated radical dosimeter that comprises a sample introduction and product collection system. In some embodiments sample introduction and product collection is supported by an automated robotic system under control of the system's instrument control high level and low level software, and control electronics subassembly. In some embodiments, the sample introduction system comprises a movable X, Y, Z robotic arm that addresses fixed sample reservoir locations upon the instrument sample deck. In some embodiments, the sample introduction system comprises a fixed inlet system and X, Y, Z moveable sample reservoirs. In some embodiments, the sample introduction system comprises a fixed inlet system and Z-r-theta movement of sample reservoirs. In some embodiments the product outlet line is distinct from the product inlet line. In some embodiments the product outlet and sample inlet lines use the same port and associated fluidic circuitry. In some embodiments the product collection system comprises a movable X, Y, Z robotic arm that addresses fixed product reservoir locations upon the instrument sample deck. In some embodiments, the product collection system comprises a fixed outlet system and X, Y, Z moveable product reservoirs. In some embodiments, the product collection system comprises a fixed outlet system and Z-r-theta movement of sample reservoirs.

Various embodiments of the invention comprise a flash photolysis system with integrated radical dosimeter that comprises a down-stream, hyphenated sample processing instrument as combined with an upstream, liquid phase molecular separation and/or analysis device. In some embodiments hyphenation is achieved using a fraction collection device. In some embodiments, the fraction collection device comprises an X, Y, Z robotic arm controlled by an automated robotic system under control of the system's instrument control high level and low level software, and control electronics subassembly. In some embodiments, the fraction collection device comprises a fixed outlet line and X, Y, Z movement of fraction collection reservoirs. In some embodiments the fraction collection device comprises a fixed outlet line and Z-r-theta movement of fraction collection reservoirs. In some embodiments, hyphenation is achieved using an in-line flow diverter. In some embodiments, the in-line flow diverter system comprises a microfluidic mixing system that automatically mixes collected sample with processing reagents, such as $H_2O_2$, glutamine, and radical dosimeter.

Various embodiments of the invention comprise a flash photolysis system with integrated radical dosimeter and microfluidics system that provides gas bubble partitioning of sample aliquots for subsequent photo-irradiation. In some embodiments, gas bubble partitioning is achieved by selective introduction of atmospheric gas using an in-line isolator assembly. In some embodiments, gas bubble partitioning is achieved by selective introduction of specific gas, such as nitrogen. In some embodiments of the invention, sample axial length and bubble axial length is controlled to create sample slugs whose axial length matches the longitudinal axis of incident light impinging upon a photolysis cell.

Various embodiments of the invention comprise a flash photolysis system with integrated radical dosimeter where the integrated radical dosimeter assembly is comprised of a free space transmission optical bench that probes the identical area as irradiated by the flash lamp photolysis source. In some embodiments, the radical dosimetry assembly is comprised of a fiber-optic transmission means that probes the identical area as irradiated by the flash lamp photolysis source. In some embodiments, the radical dosimetry assembly is comprised of a liquid core waveguide that probes the identical area as irradiated by the flash lamp photolysis source. In some embodiments, the radical dosimetry assembly probes a region of sample down-stream from the flash lamp photolysis source irradiated region, using free space, fiber optic, and/or liquid core waveguide optical means. In some embodiments, output from the radical dosimetry system is used to determine background scavenging of radicals using a radical dosimeter.

Various embodiments of the invention comprise a photolysis cell for which at least one optically illuminated surface is coated with a metal oxide catalyst that catalyzes the creation of OH radicals from water. In some embodiments, the said photolysis cell is comprised of optically transparent capillary and is illuminated by a pulsed laser pump source. In some embodiments, the said photolysis cell is comprised of an optically transparent opto-fluidic chip and is illuminated by a pulsed laser pump source.

Various embodiments of the invention comprise a photolysis cell comprising a liquid core waveguide that is used in combination with a pulsed laser pump source. In some embodiments, the photolysis cell comprises an integrated waveguide that is used in combination with a pulsed laser pump source. In some embodiments, the photolysis cell comprises a surface evanescent waveguide that is used in combination with a pulsed laser photolysis source. In some embodiments, the photolysis cell comprises a micro-structure optical resonator that is used in combination with a pulsed laser photolysis source.

Various embodiments of the invention comprise using a flash photolysis system with integrated radical dosimeter. These embodiments include a method of producing labeled protein for analysis comprising: (1) mixing protein sample with a dosimeter internal standard, whose change in measured photometric absorbance is directly related to effective hydroxyl radical yield and other required labeling reagents, (2) introducing said sample into a photolysis cell, (3) determining the nascent photometric absorbance of said sample, (4) photo-irradiating said sample with at least one burst of photolysis source light, (5) determining the change in photometric absorbance for said sample after photo-irradiation, and (6) adjusting the spectral irradiance of the photolysis source light in accordance with the change in dosimeter internal standard photometric absorbance.

Various embodiments of the invention comprise a method for producing labeled protein for analysis comprising: (1) mixing protein sample with a suspension of metal-oxide photo-catalytic particles and appropriate reagents, (2) introducing said sample into a photolysis cell, (3) photo-irradiating said sample with at least one burst of pump source light, and (4) collecting product of said photo-irradiation for subsequent analysis.

Various embodiments of the invention comprise a method for producing labeled protein for analysis comprising: (1) mixing protein sample with requisite buffer and reagents; (2) introducing said sample into a photolysis cell with at least one optical surface coated with metal-oxide photo-catalyst; (3) photo-irradiating said sample with at least one burst of pump source light, and (4) collecting product of said photo-irradiation for subsequent analysis.

Various embodiments of the invention comprise a method for producing labeled protein for analysis comprising: 1) collecting sample produced by an upstream molecular separation/analysis device using an integrated fraction collection assembly; 2) mixing collected sample with requisite reagents; 3) introducing said sample to a photolysis cell; 4) photo-irradiating said sample with at least one burst of pump source light; and (5) collecting product of said photo-irradiation for subsequent analysis.

Various embodiments of the invention comprise a method for producing labeled protein for analysis comprising: 1) hyphenating said photolysis system with an upstream molecular separation/analysis using an integrated in-line flow diverter: 2) mixing collected sample with requisite reagents using an integrated micro-fluidic mixer; 3) introducing said sample to a photolysis cell; 4) photo-irradiating said sample with at least one burst of pump source light; and (5) collecting product of said photo-irradiation for subsequent analysis.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. Further, the above objects and advantages of the invention will become readily apparent to those skilled in the art from reading the following description of some embodiments when considered in the light of the accompanying figures that incorporate features of the present invention. The components in the drawings are not necessarily to scale, emphasis instead being placed upon clearly illustrating the principles of the present disclosure.

Any of the systems or methods described herein can according to specific embodiments further comprise any one or more of the following of which.

DETAILED DESCRIPTION

Devices and methods are provided for the analysis of biomolecular higher order structure that is accomplished by selective labeling of solvent exposed molecular groups, as catalyzed by fast photo-oxidation. The devices and methods can be applicable to a variety of research fields, such as: general protein biochemistry; biopharmaceutical research and development; antibody research and development; therapeutic antibody research and development; small molecule drug research and development; and/or the like. Moreover, the devices and methods can be applicable to a variety of research analyses such as: protein-ligand interaction analysis; protein-protein interaction analysis; protein-fusion product analysis; protein conformation and conformational change analysis; small drug molecule mode of action analysis; biopharmaceutical mode of action analysis; post-transcription peptide modification analysis; fatty acid and saccharide analysis; antibody-antigen analysis; protein epitope mapping; chemical reaction monitoring; and/or the like. Further, the devices and methods can comprise a biopharmaceutical production quality control analyzer for the following pharmaceutical products: monoclonal antibodies; polyclonal antibodies; antibody-drug conjugates; bioactive proteins; therapeutic enzymes; other protein- or conjugated protein-based drugs; biomolecule structure elucidation; and/or the like.

The device can receive analytical sample for subsequent chemical labeling via a step-wise introduction of previously analyzed or purified sample by manually pipetting the sample into appropriate micro-centrifuge tubes or micro-plates that are placed into the system's sample introduction assembly. Alternatively, the device can be hyphenated with and receive sample directly from other separation and analysis instruments such as but not limited those which perform: liquid chromatography (LC), including reverse phase, normal phase, ion exchange, size exclusion, bio-recognition affinity, and hydrophilic interaction modes of separation; field-flow fractionation; capillary zone electrophoresis; and capillary isoelectric focusing electrophoresis. The before noted separation techniques may also be hyphenated with but not limited to the following detection schemes: ultraviolet, visible, and infra-red photometric absorbance; refractive index; light scattering; chemiluminescence; fluorescence; radiometric; voltametric; amperometric; mass spectrometric detection; and/or the like. Also, small samples, for example, on the order of a few microliters, containing an analyte to be measured by a device or method of the invention can be evaluated.

Figure 1:
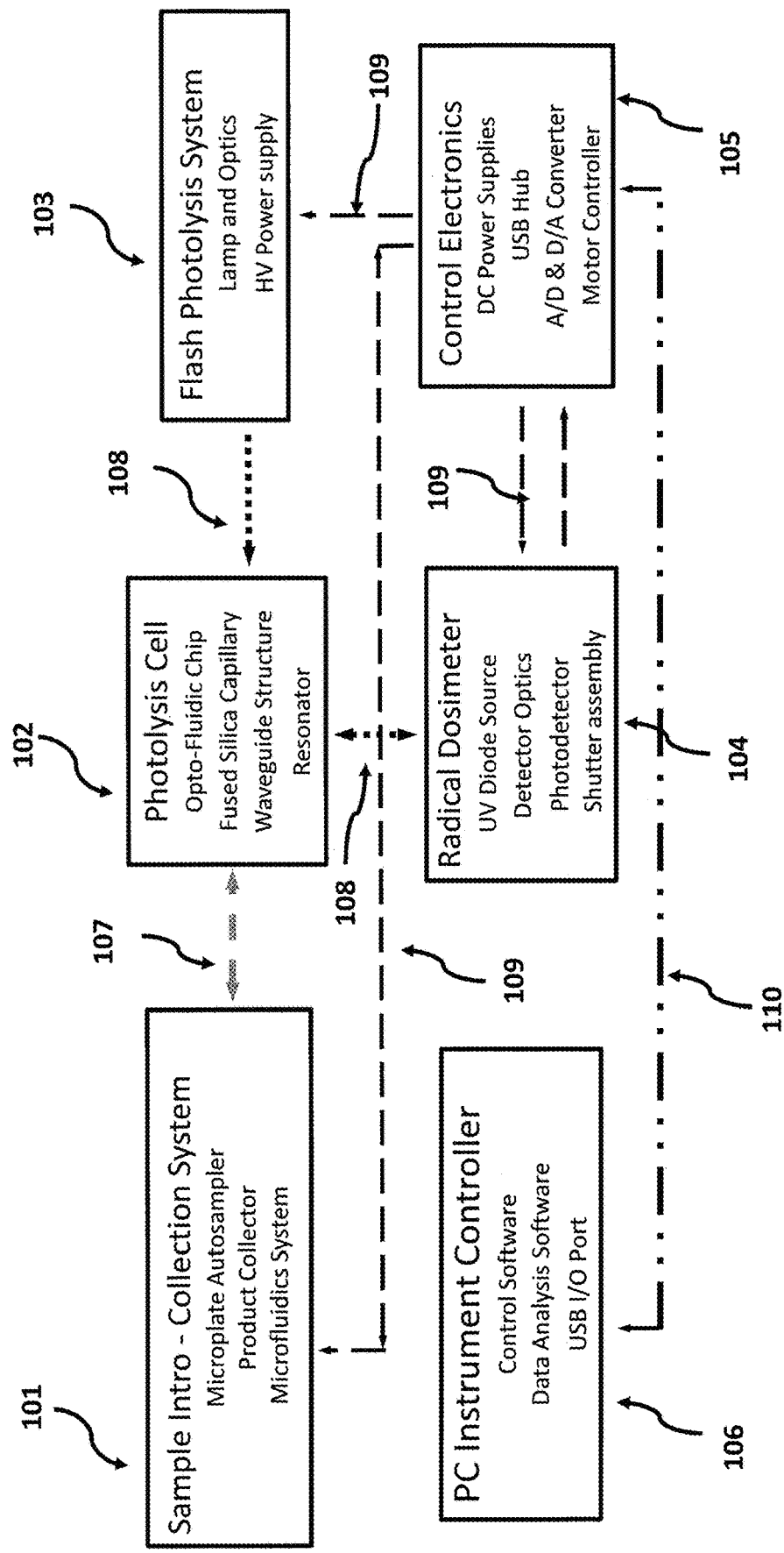
FIG. 1 is a block diagram that illustrates the various subassemblies that comprise an exemplary embodiment of the invention's flash photolysis oxidation system. Subassemblies include: sample introduction and product collection system (101); flash oxidation photolysis cell (102); flash oxidation flash lamp system and associated optics (103); radical dosimeter assembly with associated ultraviolet detector system and optics (104); system control electronics (105); and external computer instrument controller (106). Also included is a legend that differentiates the following sub-assembly interconnection pathways: fluidic lines (107); optical paths (108); analog lines (109); and digital lines (110).

In various embodiments flash photo oxidation apparatus is comprised of a number of subassemblies as illustrated in FIG. 1. Samples of interest are introduced via the sample introduction system (101). Samples can be presented using small volume micro-centrifuge tubes or by using multi-well microtiter plates as readily available from Eppendorf (Hamburg, Germany). As described elsewhere herein, the sample introduction system is combined with the product collection system (101). After exposure, photo-oxidized products are deposited into designated microtubes, microplates, or designated wells of the same microplate that was used for sample introduction. Microfluidic circuitry optionally provides the means for sample aspiration, transportation, as well as the transportation and deposition of oxidized product.

Sample photo-oxidation occurs within the instrument's photolysis cell (102). In some embodiments, a photolysis cell is comprised of a fused silica capillary as available from Polymicro Technologies—Molex (Phoenix, AZ, USA). Typical capillary internal diameter can range from 50 micrometers to 1 mm. Typical wall thickness can range from 50-100 micrometers. In some embodiments, it is desired to use capillaries constructed with substantially thicker walls such as those which have outside diameters as large as 1-5 mm and internal diameters as small as 0.1 mm. In some embodiments, opto-fluidic chips are fabricated using a variety of techniques, such as lithography assisted wet chemical etching, dry reactive ion etching, and laser ablation microstructuring and or the like that create microfluidic channels within a quartz substrate. Fluidic and optical channel internal diameter can range from 0.1, 0.3, 0.6, or 1 mm, or any range there between. In some embodiments, channel internal diameter is less than 0.1 mm. In some embodiments, fluidic and optical channels have different internal diameters to best match disparate requirements of fluid transfer and optical coupling. Moreover, the opto-fluidic chip can contain an optical wave-guiding structure, such as an integral optical fiber, monolithic waveguide, liquid core waveguide, evanescent guiding means and or the like using metal oxides, rare-earth metals, or grating structures. In some embodiments at least one sample contacting surface of the photolysis cell is coated with a photocatalytic metal oxide, such as $TiO_2$. For some photocatalytic metal-oxide formulations, photolysis can be initiated using long UV (wavelength ≥300 nm) or visible light. For these embodiments, capillaries and opto-fluidic chips can be fabricated using various varieties of glass, such as BK-7 or Borofloat® 33 (Schott AG, Germany), in lieu of fused silica or quartz. In some embodiments, quartz or glass opto-fluidic cells comprise a resonance structure to support resonance and/or multi-pass incident photon collision with dissolved reactants, such as but not limited to $H_2O_2$, suspended metal-oxide nanoparticles, or immobilized metal oxide films upon at least one sample contacting surface.

The photolysis cell (102) receives sample from the sample introduction and collection system via a microfluidic path. After processing, oxidized sample within the photolysis cell is optionally transferred into the collection system using the same transfer line that was used for sample introduction. In some embodiments, the photolysis cell has dedicated inlet and outlet fluidic transfer lines. The photolysis cell is in optical communication with two other subassemblies: the flash photolysis system (103) and the radical dosimeter (104).

The photolysis cell physically resides within the device's flash photolysis system. The photolysis system is comprised of: a plasma flash lamp, or other appropriate light source such as a laser diode; associated light collection/transmission optics; and a light source high voltage power supply. A variety of high pressure gas lamps can be used as the photolysis light source including but not limited to: mercury vapor (Hg), xenon (Xe), krypton (Kr), helium (He), neon (Ne), sodium (Na), argon (Ar), cesium (Cs), mixtures of Xe and Kr, mixtures Na and Hg, mixtures of Cs and Hg, mixtures of Hg or Xe with the addition of metal halides, and/or the like. Plasma gas composition is selected based upon desired photolysis light source spectral irradiance. In some embodiments, the flash lamp is comprised of Kr, Xe, or a blend of Kr and Xe gas in a high pressure format, for which the enclosed gas is contained within the flash lamp envelope at elevated pressure ranging from 2-14 bar. Flash lamp plasma is created by an electrode assembly housed within the lamp envelope. Cathode and anode components of the electrode assembly are fabricated from conductive metals with good work function and structural integrity to minimize thermal evaporative damage and surface ablation by the resultant plasma, thus extending lamp life. Suitable electrode materials in pure or alloy form include: tungsten (W), thorium (Th), molybdenum (Mo), iron (Fe), niobium (Nb), and zirconium (Zr). In some embodiments, the anode is comprised of 2% thoriated tungsten, and the cathode is comprised of porous tungsten. Cathode—anode arc distance is prudently established to match the requirements of the light transmission means to the photolysis zone. In some embodiments, the electrode gap distance ranges from 0.5-2 mm. In some embodiments, the electrode gap distance ranges from 2-5 mm.

The envelope of the flash lamp is comprised of optically transparent material such as Suprasil® quartz (for low UV transmission >180 nm), clear fused quartz (for UV transmission >220 nm), or glass (for long UV and visible transmission >300 nm). As further described elsewhere herein, light from the lamp's plasma arc is directed towards the photolysis cell using one of the following optical means: imaging optics (601), collection optics (702) and/or non-imaging optics (803), each with its associated optical components. Optical components include but are not limited to lenses (planar-convex, bi-convex), mirrors (planar, parabolic, and elliptical), and wave-guiding structures, such as optical fibers or monolithic waveguides and or the like. The plasma flash lamp is driven by a high voltage controller comprised of a high voltage power supply, trigger transformer assembly, klystron assembly, and analog control circuitry and or the like. The flash lamp drive circuitry receives DC power and analog control from the control electronics subassembly (105).

The radical dosimeter (104) transmits photometric absorbance incidence light to and receives photometric absorbance transmitted light from the photolysis cell. For the photometric absorbance light source, selective, narrow-bandwidth (≤15 nm) UV light is generated by a UV light source (2401) and is directed to probe the photolysis cell (102) in the region illuminated by the flash lamp source. When used in combination with an optical notch filter that passes light of suitable wavelength, applicable UV light sources include broad spectrum sources such as Hg, Xe, or deuterium (D) plasma lamps. Alternatively, narrow bandwidth, solid state light emitting diode (LED) sources can be employed. In some embodiments, a 260 nm UV LED source is used such as available from Thorlabs (Newton, NJ, USA). As is described elsewhere herein, light from the UV light source can be transmitted into the photolysis cell (102) using a plurality of approaches including: collimated light transmitted through free air; transmission via coupling to an optical fiber of appropriate composition and numerical aperture; and transmission using a liquid core waveguide. After probing the photolysis zone, light is directed to impinge upon a photodetector using the above noted transmission device. In some embodiments, the photodetector (2403) comprises a silicon photo-diode assembly with optical transmission and photon-to-electron conversion efficiency in the wavelength domain of interest, such as the S1336-8BQ silicon photodiode available form Hamamatsu (Hamamatsu City, Japan). Photodiode output current is processed by a current to voltage (I to V) convertor, to provide a voltage that is proportional to photodiode incident light intensity. Photodiode output voltage is transmitted to the control electronics assembly (105), where an analog to digital converter (ADC) creates a digital signal that is ultimately transmitted to the PC instrument controller (106) where UV absorbance calculations are performed. The Radical dosimeter (104) further comprises a shutter assembly that protects the photodetector elements from pump source high intensity light. The shutter is closed during the pump source flash and is opened during the probe source measurement cycle.

The control electronics assembly (105) functions to: provide direct current (DC) drive voltage, derived from laboratory alternating current (AC) power sources, (to peripheral assemblies); provide analog and digital control signals to peripheral devices; receive analog or digital information from peripheral devices; provide ADC and digital to analog conversion (DAC) functions; and provide data to and receive commands from the PC instrument controller (106). In some embodiments, the control electronics (105) assembly comprises a motor controller that interfaces with motors located within the sample introduction-collection system (101). Moreover, the control electronics assembly, in such embodiments, optionally contains a universal serial bus (USB) hub for digital communication with the PC instrument controller.

The PC instrument controller (106) functions to provide process control for various instrument peripheral devices while receiving status and data information from these devices in digital format. In some embodiments, the PC instrument controller (106) runs a software control program with two main modules: a low level, multi-threaded module for instrument component control and a high level user interface (UI) module. In some embodiments, the control electronics assembly (105) comprises an embedded microprocessor that provides low level instrument component control while communicating with a high level UI control program of the PC instrument via a USB interface.

Not shown in FIG. 1 is a safety interlock system. The safety interlock system functions to protect users from unwanted exposure to UV irradiation or high voltage. Moreover, the interlock system also insures that system operation only proceeds when all required components are on-board. The safety interlock system provides an analog control signal to the control electronics assembly (105). In some embodiments, the control signal comprises a closed or conductive circuit of low resistance (<1 ohm). In some embodiments, the control signal comprises a transistor-transistor-logic (TTL) signal. When the system's protective coverings that enclose the flash lamp and radical dosimeter source assemblies and associated high voltage power supplies are in place, sensors detect their presence. Exemplary sensors include but are not limited to contact closure switches, magnetic Hall sensors, light optical interrupters, and electric conductivity sensors and or the like. Housing in place signals trigger a "go state" to the safety interlock system, which in turn provides a go signal go to the control electronics assembly, enabling flash photolysis lamp, photometric absorbance lamp, and high voltage power supply operation. In some embodiments, a sensor detects the presence of the photolysis cell (102) within the flash photolysis system (103). When the photolysis cell is in place, a go signal is generated. Should the photolysis cell not be installed, the lack of a go signal results in a cell-not-in-place signal communicated to the user via the instrument controller (106) user interface (UI) program. The photolysis cell not-in-place signal further inhibits operation of the sample introduction-collection system (101) and flash lamp power supply (103). Similar go signals are generated by sensors that detect the presence of sample inlet reservoirs, product collection reservoirs, and reagent reservoirs.

As previously described and illustrated in FIG. 1, samples of interest are introduced via the sample introduction/product collection system (101). Samples can be presented using small volume micro-centrifuge tubes, by using multi-well microtiter plates as readily available from Eppendorf (Hamburg, Germany), or other methods known in the art for introducing small samples. The sample introduction system (101) is combined with the product collection system to comprise an integrated sample introduction and product collection system assembly, and can be used for both functionalities. After exposure, photo-oxidized products are deposited into designated microtubes, microplates, or designated wells, optionally of the same microplate that was used for sample introduction. In some embodiments, microfluidic circuitry is configured to perform sample aspiration, transportation, as well as the transportation and deposition of oxidized product.

Figure 2:
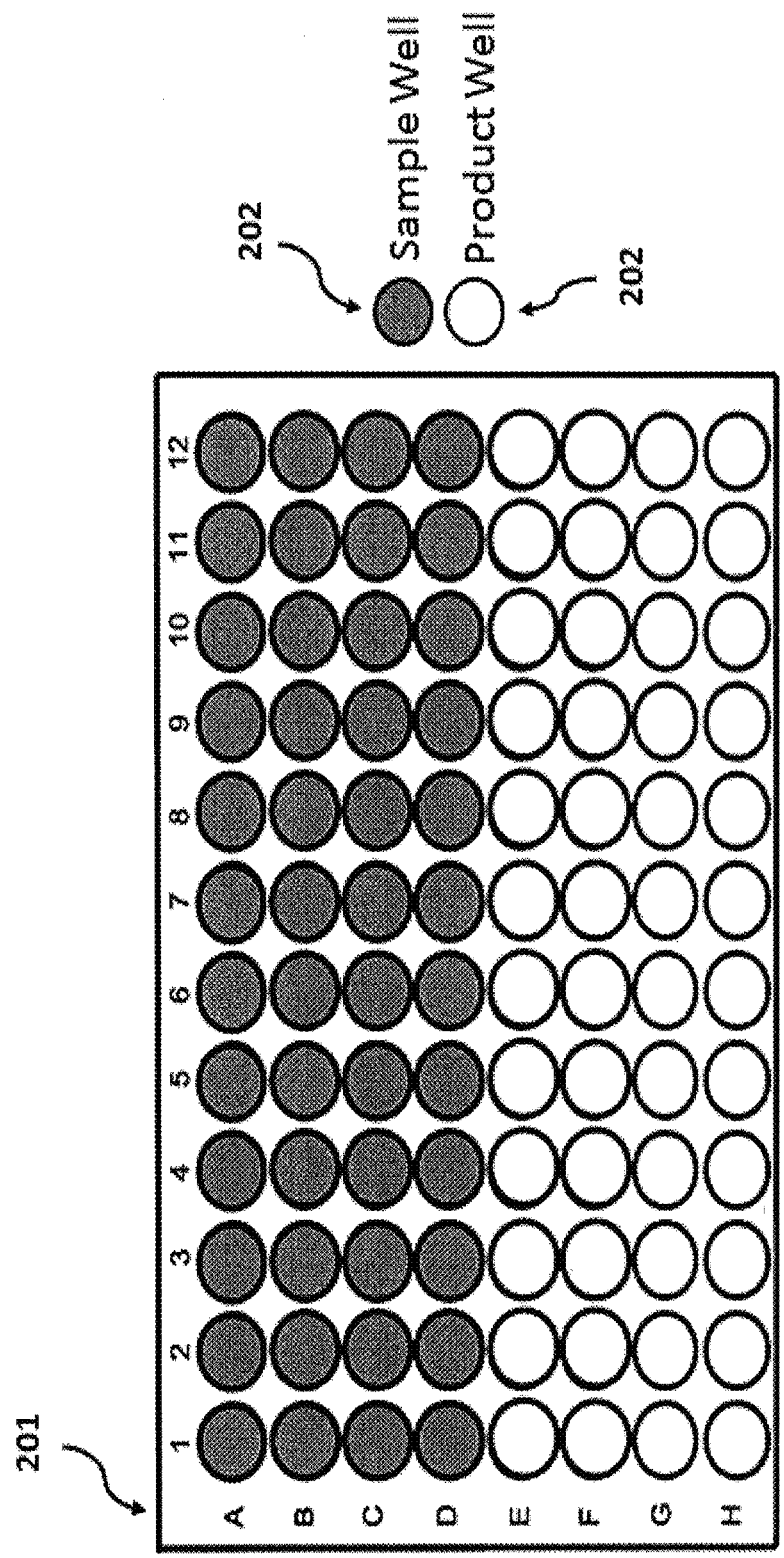
FIG. 2 depicts an exemplary sample introduction and product collection means embodied in the present invention that comprises a 96-well microplate (201), according to various embodiments. Both sample wells (202) and product wells (203) are illustrated.

In some embodiments, a robotic autosampler is used to facilitate semi-automatic or automatic introduction of liquid sample and/or collection of liquid product. In some embodiments, sample introduction and product collection vessels can be in the form of a 96-well micro-plate (201). These fluidic vessels are housed in the robotic autosampler assembly. In some embodiments, a sample introduction inlet line and product delivery line is moved about by an autosampler robotic arm. Three-dimensional (left/right; front/back; up/down; i.e. XYZ) robotic arm motion is actuated using motors and associated mechanical linkage and positional sensors. Motor control is provided by the control electronics assembly (105). As shown in FIG. 2, the robotic arm is moved to selectively aspirate sample from a sample well (202) or deposit product into a designated product well (203) as located in a fixed position on the autosampler sample deck. In an exemplary embodiment, sample aspiration and product delivery is accomplished using a common fluid transfer line.

In some embodiments, the XYZ motion of the robotic arm is replaced by XYZ motion of the sample deck containing the sample and product fluidic vessels. Vessels are elevated to a common inlet-outlet port using an elevator (Z direction). Vessel selection is accommodated by X, Y motion of the sample deck. In some embodiments, XYZ motion is replaced by a Z-R-theta stage in which sample vessels are elevated to a common inlet-outlet port. Vessel selection is achieved by rotating the sample deck (theta) at a given radius of rotation (R) with respect to the port.

Hyphenation With Upstream Device

In some embodiments, the sample introduction system is hyphenated with an up-stream fluidic separation device such as but not limited those which perform: liquid chromatography (LC), including reverse phase; normal phase, ion exchange, size exclusion, bio-recognition affinity employing antibody, aptamer, lectin, or molecular imprint affinity sorbents, and hydrophilic interaction modes of separation; field-flow fractionation; capillary zone electrophoresis; and capillary isoelectric focusing electrophoresis. The before noted separation techniques may also be hyphenated with but not limited to the following detection schemes: ultraviolet, visible, and infra-red photometric absorbance; refractive index; light scattering; chemiluminescence; fluorescence; radiometric; voltametric; amperometric; and mass spectrometric detection. When upstream-detection is employed, automated hyphenation can be achieved using a fraction collector or in-line flow diverter.

Fraction Collection System

Figure 3:
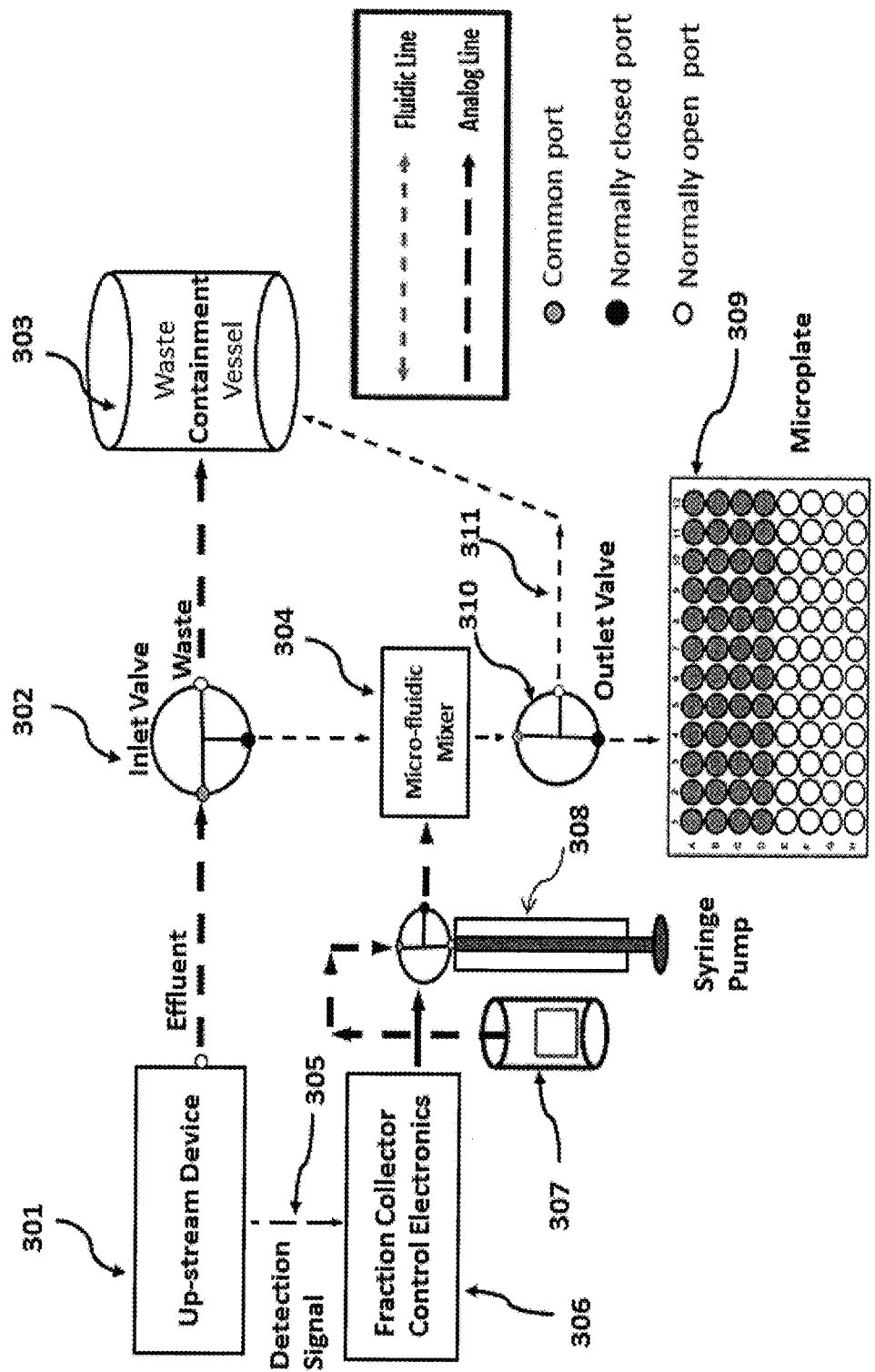
FIG. 3 illustrates an exemplary hyphenation system using an integrated fraction collector, according to various embodiments. The following elements are depicted: upstream molecular separation and analysis device (301), inlet diverting valve (302), waste containment vessel (303), microfluidic mixer (304), upstream device detection signal (305), fraction collector control electronics (306), $H_2O_2$ and other reagent reservoir (307), syringe pump (308), sample/product microplate (309), outlet diverting valve (310), and outlet waste stream (311).

A fraction collection system is illustrated in FIG. 3. Effluent from the upstream device (301) is directed towards an inlet 3-way valve (302) that directs effluent flow to waste (303) or into a micro-mixer (304). When the up-stream detection device detects the eluted compound of interest, a detection signal (305) is transmitted to the fraction collector control electronics (306). After a first pre-determined delay period, the fraction collector control electronics initiates the flow of aqueous hydrogen peroxide (307) from a syringe pump (308). $H_2O_2$ is mixed with the compound of interest using the micro-fluidic mixer and, after a second predetermined delay period, the mixture is deposited into the autosampler microplate (309) by diverting outlet valve (310) flow from the fraction collector waste line (311) to the microplate. The duration of the first delay period is determined by: the flow rate of the upstream device; the internal diameter and length of the connecting fluidic line that extends from the outlet of the upstream device to the inlet of the fraction collector; and the fraction collector internal volume that extends to the 3-way diverter valve; and can be automatically calculated by the system's higher order control program with user input values for flow rate and transfer line dimensions. The duration of the second delay period is determined by the flow rate of the up-stream device, flow rate of the syringe pump, and fraction collector internal volume, including the micro-fluidic mixer. The second delay period can be automatically established by the system's high order control program with user input value for the up-stream device flow rate. All other essential elements are inherent and known attributes of the fraction collection device. Both three-way valves are selectively actuated by the fraction collector control electronics with input from the high order and low order control software programs.

In some embodiments, the use of $H_2O_2$ is obviated by employing photocatalytic metal oxides. In this embodiment, $H_2O_2$ reservoir (307), syringe pump (308), and micro-fluidic mixer (304) are not required. In some embodiments, aqueous $H_2O_2$ is included in the running buffer/mobile phase of the upstream device, circumventing the need for the $H_2O_2$ reservoir and syringe pump, as well as the microfluidic mixer. In some embodiments, aqueous $H_2O_2$ is pre-deposited into the fraction collector wells of the autosampler microplate prior to receiving sample from the upstream device and mixing occurs via passive diffusion. In some embodiments, the fraction collector autosampler microplate is mounted to an agitator that actively agitates the mixture of pre-deposited $H_2O_2$ and collected sample.

In-Line Flow Diverter System

Figure 4:
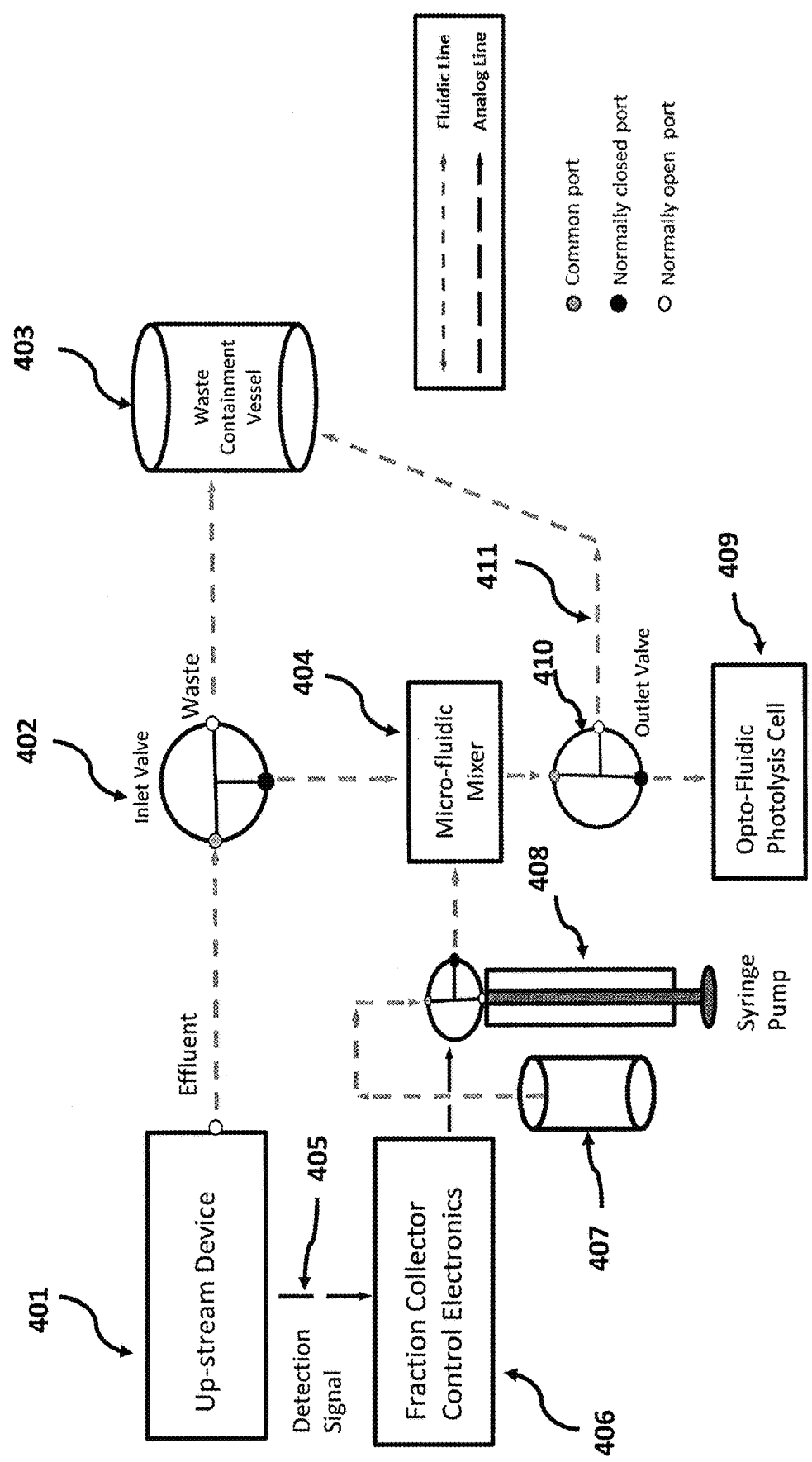
FIG. 4 depicts an in-line flow diverter hyphenation scheme, according to various embodiments. Illustrated are: upstream molecular separation and analysis device (401), which is an embodiment of (301); inlet diverting valve (402), which is an embodiment of (302); waste containment vessel (403), which is an embodiment of (303); microfluidic mixer (404), which is an embodiment of (304); up-stream device detection signal (405), which is an embodiment of (305); fraction collector control electronics (406), which is an embodiment of (306); reagent reservoir (407), which is an embodiment of (307); syringe pump (408), which is an embodiment of (308); opto-fluidic photolysis cell (409); outlet diversion valve (410), which is an embodiment of (310), and outlet waste stream (411), which is an embodiment of (311).

An in-line flow diverter system is illustrated in FIG. 4. Effluent from the upstream device (401) is directed towards an inlet 3-way valve (402) that directs effluent flow to waste (403) or into a micro-mixer (404). When the up-stream device (401) detects the eluted compound of interest, a detection signal (405) is transmitted to the fraction collector control electronics (406). After a first pre-determined delay period, the fraction collector control electronics initiates the flow of aqueous hydrogen peroxide (407) from a syringe pump (408). $H_2O_2$ is mixed with the compound of interest using the micro-fluidic mixer (404) and, after a second predetermined delay period, the mixture is transferred to the opto-fluidic photolysis cell (409) by diverting outlet valve (410) flow from the fraction collector waste line (411). After a third delay period that commences at the actuation of the outlet valve, the outlet valve is switched back to its normally open position, and the photolysis cycle is initiated, creating photo-oxidized product. The duration of the first delay period is determined by: the flow rate of the upstream device; the internal diameter and length of the connecting fluidic line that extends from the outlet of the upstream device to the inlet of the fraction collector; and the fraction collector internal volume that extends to the 3-way diverter valve; and can be automatically calculated by the system's higher order control program with user input values for flow rate and transfer line dimensions. The duration of the second delay period is determined by the flow rate of the up-stream device, flow rate of the syringe pump, and fraction collector internal volume, including the micro-fluidic mixer. The second delay period can be automatically established by the system's high order control program with user input value for the up-stream device flow rate. All other essential elements are inherent and known attributes of the fraction collection device. The duration of the third delay period is dependent upon internally fixed parameters and is optionally automatically determined with a priori knowledge of the second delay period parameters. Both three-way valves are selectively actuated by the fraction collector control electronics with input from the high order and low order control software programs.

In some embodiments, the use of $H_2O_2$ is obviated by employing photocatalytic metal oxides. In this embodiment, $H_2O_2$ reservoir (407), syringe pump (408), and micro-fluidic mixer (404) are not required. In some embodiments, aqueous $H_2O_2$ is included in the running buffer/mobile phase of the upstream device, circumventing the need for the $H_2O_2$ reservoir and syringe pump, as well as the microfluidic mixer.

Sample Introduction and Collection System: Fluidics

Sample Introduction

Figure 5:
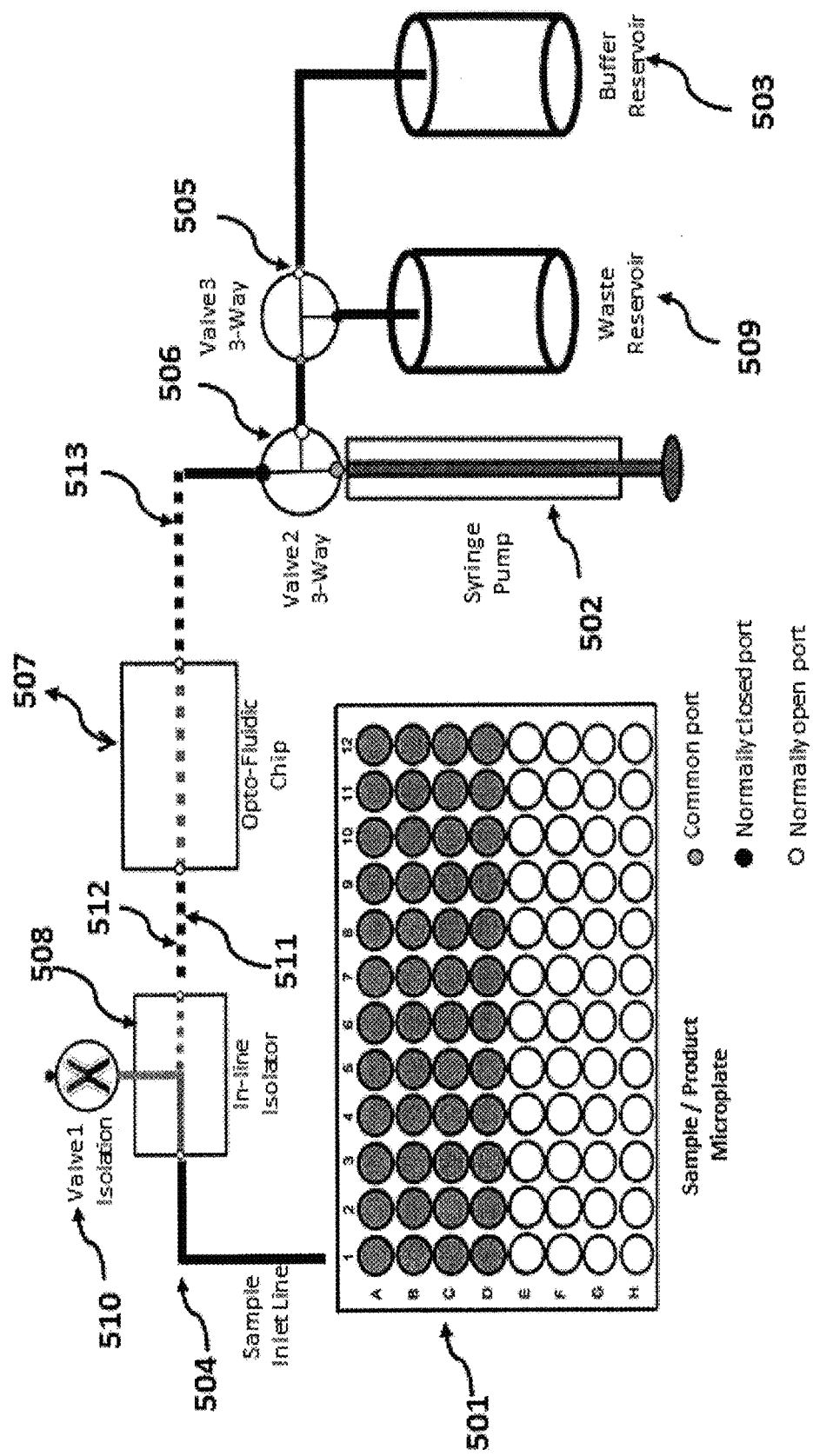
FIG. 5 illustrates the microfluidics system, according to various embodiments. Depicted are: sample introduction and product collection microplate (501), syringe pump (502), buffer reservoir (503), sample inlet line (504), $V_3$ three-way valve (505); $V_2$ three-way valve (506), opto-fluidic chip (507), in-line isolator (508), waste reservoir (509), $V_1$ isolation valve (510), sample isolating bubble (511), isolated sample slug (512), and photolysis product stream (513).

Distinct from the above described microfluidic circuitry in FIGS. 3 and 4, the sample introduction/product collection system (101) has a dedicated microfluidic circuit as illustrated in FIG. 5. In sample introduction mode, samples are aspirated from designated locations within a microplate (501). Alternatively, samples could be withdrawn from any other vessel including but not limited to microtubes and larger reservoirs and or the like. Sample containing reservoirs could be manually filled by the user and placed upon the system's autosampler deck. Alternatively, samples may be deposited into their designated reservoir location by the system's automated fraction collector operating in concert with an upstream device.

Samples are drawn into the fluidic circuit using a syringe pump (502). The system is primed using priming buffer as pumped from a buffer reservoir (503), so that the microfluidic lines extending from the syringe pump (502) to the sample inlet line (504) are filled with buffer. In this fashion, fluid transfer from the sample plate is enabled by using a liquid-liquid junction. During the initial phase of the prime cycle, 3-way valve $V_3$ (505) is de-energized to permit communication between the syringe pump assembly and the buffer reservoir. During this operation, valve $V_2$ (506) is energized, enabling communication between the syringe bore (502) and valve $V_3$ (505), thus allowing the syringe bore to be filled with priming buffer. During the final phase of the prime cycle, $V_2$ (506) is de-energized allowing for communication from the syringe pump to the sample inlet line, and the syringe pump is driven to pump fluid through the opto-fluidic chip (507) and in-line isolator (508). Excess buffer that flows out of the sample inlet line is captured within a waste reservoir located on the autosampler deck. After priming, the syringe pump's remaining contents are delivered to a waste reservoir (509), by energizing valves $V_2$ and $V_3$ and driving the syringe pump to the full extent of its bore. Sample is aspirated into the circuit by the fill cycle of the syringe pump with valve $V_2$ in its normally open state.

In some embodiments, aspirated sample flows into an in-line isolator (508). In the isolator assembly, sample fluid can be segmented into finite slugs of sample (512) by gas bubbles (511) introduced by isolation valve $V_1$ (510). Valve $V_1$ is selectively energized, allowing for the introduction of gas to create a segregating bubble within the aspirated sample stream. Partitioning gas can be atmospheric gas as aspirated by $V_1$ or it can be a purified, inert gas such as nitrogen. The open state of $V_1$ is under microprocessor control, enabling a desired number and length of bubble partitions. In this embodiment, bubble partitions are introduced as to create a sample slug whose linear length closely approximates the photo-irradiation axial distance generated by the flash lamp light as focused upon the transparent fluidic channel of the opto-fluidic chip (507). The bubble partition reduces unwanted mixing between irradiated sample (oxidized product) and non-irradiated sample, as the new sample is photo-oxidized and product is subsequently transferred. Gas bubble partitions function to create a surface tension barrier which prevents unwanted mixing of product and unprocessed analyte via axial diffusion.

Product Delivery

In the described embodiments, the sample introduction/photo-oxidation process proceeds for a user-defined number of cycles for a given sample of interest. Oxidized products from multiple trials are partitioned using gas bubbles, and, with each photolysis cycle, are progressively moved down the fluidic circuit towards valve $V_2$ (506) within a fluidic transfer line (513). The fluidic transfer line (513) is of sufficient length and internal diameter to accommodate a plurality of product cycles. Transfer line lengths range from, but are not limited to, 100 mm-1000 mm. Transfer line internal diameters range from, but are not limited to, 0.100 mm to 0.600 mm.

Upon completion of the photo-oxidation process, photo-oxidized products are moved back up the fluidic circuit to be deposited within their respective collection reservoirs. In some embodiments, sample introduction and product delivery are accomplished using the same fluidic line and circuitry as depicted in FIG. 5. For product deposition, the operational cascade is as follows. Syringe pump (502), valves $V_2$ (506) and $V_3$ (505) are operated to fill the syringe pump bore with buffer from reservoir (503). $V_2$ is de-energized and the syringe pump is used to pump buffer into the transfer line (513). Pumping continues as product is transported through the opto-fluidic chip (507), in-line isolator (508), and through the sample inlet line to be deposited into a pre-determined product reservoir such as a well within the sample/product microplate (501). Product transfer is complete when the photo-oxidized product housed within the fluidic circuit is deposited into the product reservoir. In some embodiments, the system's control software tracks the total volume of aspirated fluid from the first photo-oxidation cycle to the last. Moreover, the inlet transfer volume that extends from the entrance of the sample inlet line to the photolysis zone of the opto-fluidic chip is known and is also considered. During product delivery, the last in and first out solution is the inlet transfer volume. The inlet transfer volume is deposited into a waste reservoir located on the sample deck. In some embodiments, the waste reservoir is a dedicated collection vessel. In some embodiments, the waste reservoir is a designated well within the sample/product microplate. Once the inlet transfer volume has been dispensed, photo-oxidized product is then delivered into its designated collection reservoir.

Flash Photolysis System

The flash photolysis system (103) serves to generate, collect, and direct UV and visible photo-excitation light into the photolysis cell. A plurality of embodiments are presented here that can be used for this purpose, with advantages and disadvantages to each. Unlike a laser, which emits a highly directional beam of minimal angular extent, a plasma flash lamp creates a light emitting volume of finite and significant extent that emits more or less non-directionally as dictated by the emission characteristics of its plasma. As such, it is desired to collect as much of this emitted light as possible and transfer it to a region of interest (i.e. a photolysis cell), necessitating collection of light over a large solid angle at the plasma source.

One consideration in designing a light collection apparatus is that plasma arcs generally will be spatially and angularly inhomogeneous with radiance distributions influenced by its arc gap length and total plasma energy, among other influences. Relative to small gap plasma arcs (i.e. 0.5-1.5 mm in length), larger plasma arcs may be more uniform in radiance over a larger hot spot, or "eye," and so may be more readily aligned to a target of interest, producing a more uniform irradiance distribution at the target. For a given plasma energy, however, these advantages come at a cost of reduced irradiance at the target.

As previously noted, the photolysis cell comprises a target region with an internal diameter as small as 0.1 mm. As such, it is desirable to collect and focus as much of the plasma light down to an image that can be formed within the photolysis cell internal diameter. To achieve the latter, a small arc plasma source is desired. On the other hand, in order to optimize the volume of produced product, the axial length of the photolysis zone should be maximized up to the limit as defined by the spectral irradiance requirement to generate hydroxyl radicals. For FPOP analysis using $H_2O_2$, the spectral irradiance requirement has been established at $\geq 3$ mJ/mm$^2$-nm. For a 0.1 mm photolysis cell internal diameter, the volume of irradiated sample is 7.85 nL per mm of length. In order to process 10 uL of sample into oxidized product, the 0.1 mm diameter×1 mm length system would require about 1,300 cycles. At a typical cycle rate of 2.0 Hz, the processing of a single sample would require about 650 seconds or just under 11 minutes, making the processing time for a 96-well or 384-well microtiter plate quite long and impractical. So, various embodiments are configured such that generated flash lamp irradiance is maximally transmitted to the photolysis cell while illuminating a suitable length of the photolysis cell.

Flash Photolysis System: Imaging Optics

Figure 6:
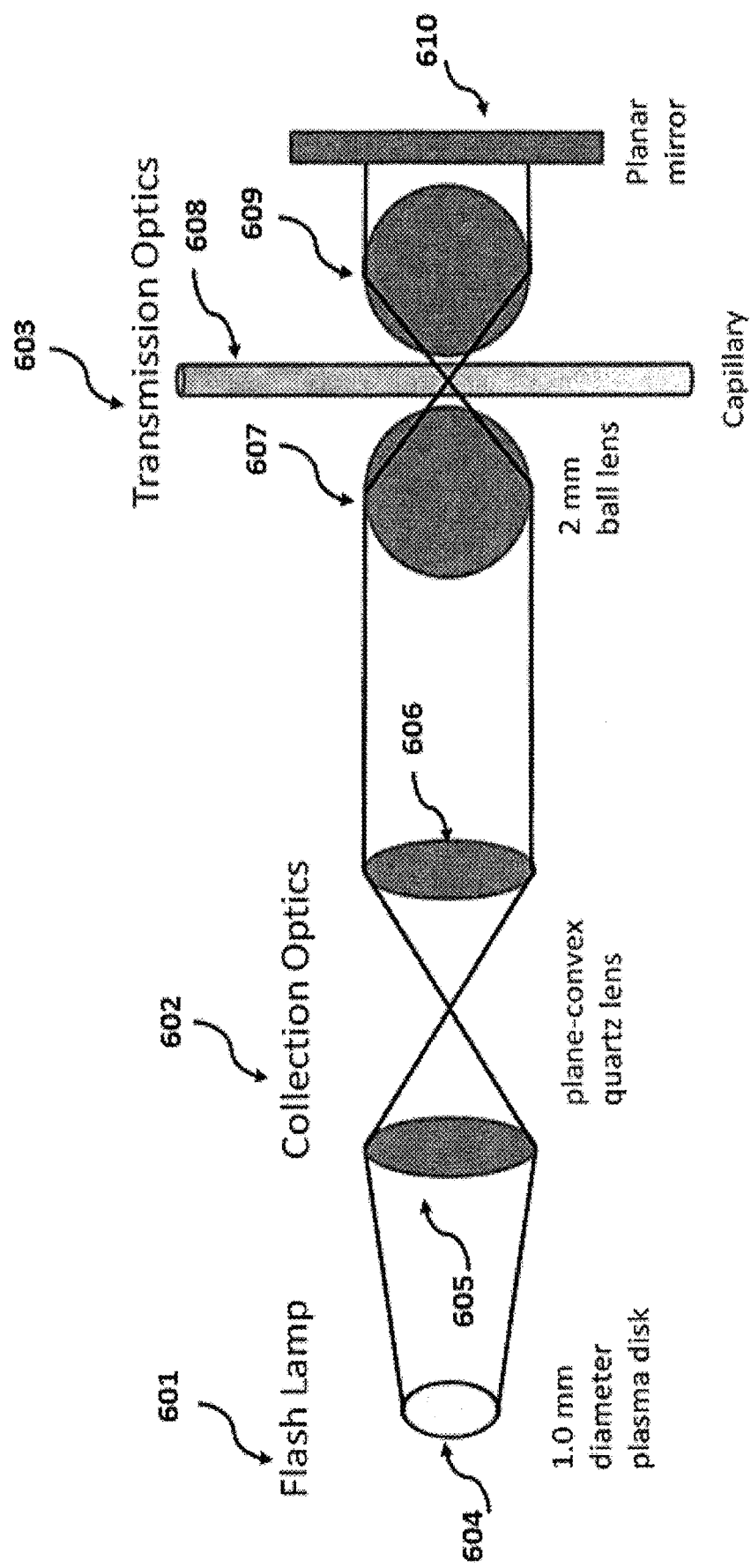
FIG. 6 illustrates an imaging flash lamp optical bench, according to various embodiments. Depicted are: flash lamp region (601), collection optics assembly (602), transmission optics region (603), flash lamp plasma disk (604), planoconvex lenses (605 & 606), ball lenses (607 & 609), capillary photolysis cell (608), and mirror (610).

In some embodiments, the flash photolysis system employs a flash lamp imaging optical system as depicted in FIG. 6. Light created by a flash lamp (601) is collected by a lens stack of collection optics (602) and ultimately imaged into the photolysis cell by transmission optics (603). Flash lamp light is collected from a single side, and as such is viewed as a disk of light (604), much as the sun or moon is viewed in the sky. In some embodiments, the collection optics comprises at least two plano-convex lenses for which the first lens (605) has its convex side directed towards the plasma disk and the final lens (606) having its convex side facing the photolysis cell. In some embodiments, the collection optics comprises at least two bi-convex lenses. In some embodiments, a plurality of lenses, differing in form and focal power, may be arranged in a stack to maximize light collection from the plasma disk and subsequent transfer to the capillary. Collimated light is transmitted through air from the collection optics to the first lens of the transmission optics assembly (607). Alternatively, light could be launched into an optical fiber of appropriate size and numerical aperture and thusly directed to the transmission optics.

The transmission optics assembly depicted in FIG. 6 is comprised of a pair of small diameter UV transparent ball lenses (607 & 609), a fused silica capillary that serves as the photolysis cell (608), and a planar mirror (610) that serves to redirect exiting light back into the photolysis cell. In this arrangement, the axial distance of the photolysis zone will be defined by the image distribution of the ball lens assembly, which in turn is matched to the capillary's internal diameter. Thus, for a 0.1 mm internal diameter capillary, the axial distance will be about 0.1 mm resulting in a photolysis volume of about 0.8 nL. For this embodiment, a preferred electrode gap distance and resultant plasma disk is taken to be about 1.0 mm. In some embodiments, a larger diameter capillary and associated larger diameter ball lenses could be used to increase photolysis zone axial length. For instance, a 1 mm internal diameter capillary and a pair of 5 mm diameter ball lenses could be used to create a 1 mm photolysis zone axial length, with a resultant volume of about 785 nL. In some embodiments, a 1.5 mm diameter electrode gap flash lamp is combined with appropriate collection optics and a transmission optics assembly that utilizes a pair of cylindrical lenses in lieu of the ball lens assembly. In this embodiment, the cylindrical lenses are arranged with their long focal axes parallel to the capillary, so that flash lamp plasma is focused within the capillary internal diameter for an extended axial length of around but not limited to 1.5-2.0 mm. In this manner, axial length can be increased without an appreciable increase of capillary diameter, minimizing spectral irradiance reduction. For the previously described embodiments, light which exits the photolysis zone is directed back by a planar mirror (610). In this fashion, back reflection effectively doubles absorbance path-length and effectively doubles the spectral irradiance, both of which improve overall OH radical yield and subsequent protein labeling. In some embodiments, the planar mirror and ball lens (609) are replaced by a spherical mirror. In some embodiments, capillary (608) is replaced by an opto-fluidic chip of previously described substrate composition and channel (fluidic/optic) properties.

Flash Photolysis System: Collection Optics

Figure 7:
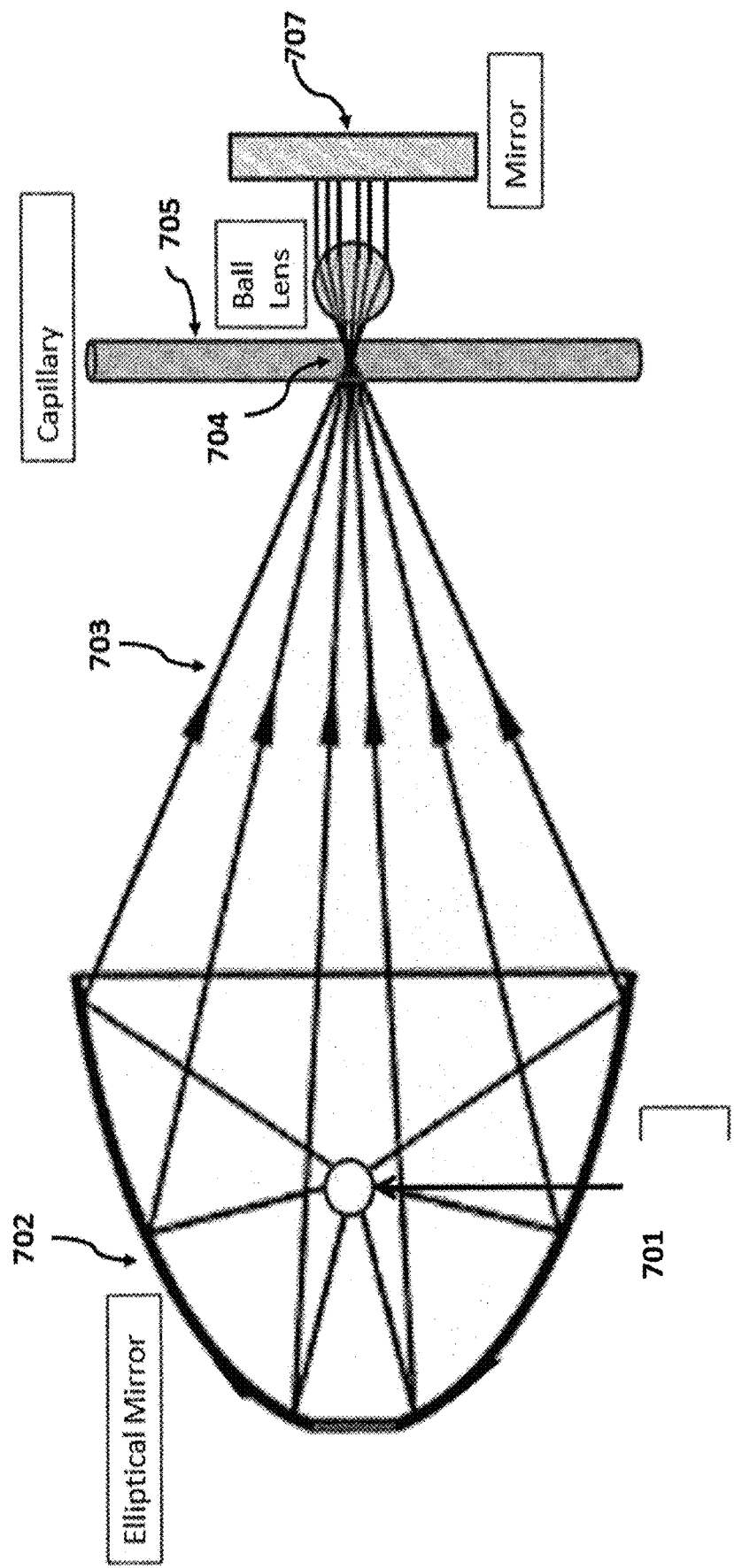
FIG. 7 depicts a flash lamp collection optics system, according to various embodiments. Shown are: lamp plasma (701), elliptical collection mirror (702), collected and transmitted flash lamp light rays (703), relayed image of the lamp plasma (704), capillary photolysis cell (705), ball lens (706), and mirror (707).

FIG. 7 illustrates a photolysis system employing flash lamp collection optics. In these embodiments, flash lamp plasma (701) is positioned at the focal point of a collecting mirror (702). Suitable collecting mirrors include but are not limited to parabolic and elliptical mirrors. Parabolic mirrors function to collect light dispersed from a source point at its focus and transmit it as a collimated beam. An elliptical mirror functions to collect light dispersed from a source at one of its foci and subsequently focus that light to a finite object or image distribution at its other focus. As an elliptical mirror functions to both collect and focus light, it represents a simplified embodiment. FIG. 7 depicts the use of an elliptical collection mirror (702). Collected light (703) is focused to an image distribution (704) within a capillary photolysis cell (705). Exiting light is collimated by a ball lens (706) and back reflected by a mirror (707). In some embodiments, capillary (705) is replaced by an opto-fluidic chip. In some embodiments, ball lens (706) and mirror (707) are replaced by a spherical mirror.

As described elsewhere herein, some embodiments include a system in which generated flash lamp irradiance is maximally transmitted to the photolysis cell while illuminating a suitable length of the photolysis cell. In the collection optics schemes discussed, photolysis cell axial length is determined by the focal distribution of the employed optical components. As such, photolysis cell image size is limited as it is in the before noted imaging optical schemes. In some embodiments, collection mirror (702) is comprised of an astigmatic elliptical mirror that focuses in a manner akin to that of a cylindrical lens. The mirror is aligned to produce a line focus at the photolysis cell, with the focal line aligned to the axis of the photolysis cell. In this manner, a long skinny optical image can be created, prudently increasing the irradiation length of a photolysis cell with an appreciably small internal diameter.

Flash Photolysis System: Non-Imaging Optics

An improvement to the efficiency of collection optics can be made by employing the design forms of non-imaging optics, as taught, for example, by Minano et al. (U.S. Pat. No. 6,639,733 B2); Hinterberger, H. and R. Winston, *Efficient Light Coupler for Threshold Čerenkov Counters*, Review of Scientific Instruments, 1966; Canavarro, D., J. Chaves, and M. Collares-Pereira, *A novel Compound Elliptical-type Concentrator for parabolic primaries with tubular receive*, Solar Energy, 2016; and Winston, R., J. C. Minano, and P. Benitez, *Nonimaging Optics,* 2005, Elsevier Academic Press. Here we uniquely make use of non-imaging optics as applied to the field of flash photolysis to maximize collection of energy emitted by an arc lamp source and to deliver this energy to a target volume where flash photolysis takes place.

With this design approach, mirrors, lenses and other optics are shaped and positioned not to form stigmatic images of the source but rather to maximize collection of light into a prescribed finite volume or through a prescribed finite surface. The relaxation of the requirement to form images of the source allows for greater freedom in design and ultimately greater light collection efficiency and potentially lower cost.

Non-imaging optics are found in a wide variety of design forms. One example of an all-reflective concentrator is known as the compound parabolic concentrator, or CPC, this form of concentrator is commonly used in solar collectors, as it is an optimal form for collecting light that enters the collector with near parallel light rays. Another exemplary form of non-imaging collector takes the shape of a compound ellipse. Other forms of compound surface are those based on hyperbolic sections and those employing refractive elements. For the purposes of this application, all specific shapes and forms of reflecting, refracting or diffracting components employed separately and in combination under the design principles of non-imaging optics are considered exemplary of the application of non-imaging optics principles to the design of light collecting optical systems in the application of producing maximal irradiation to a flash photolysis target volume from an arc lamp source.

Figure 8:
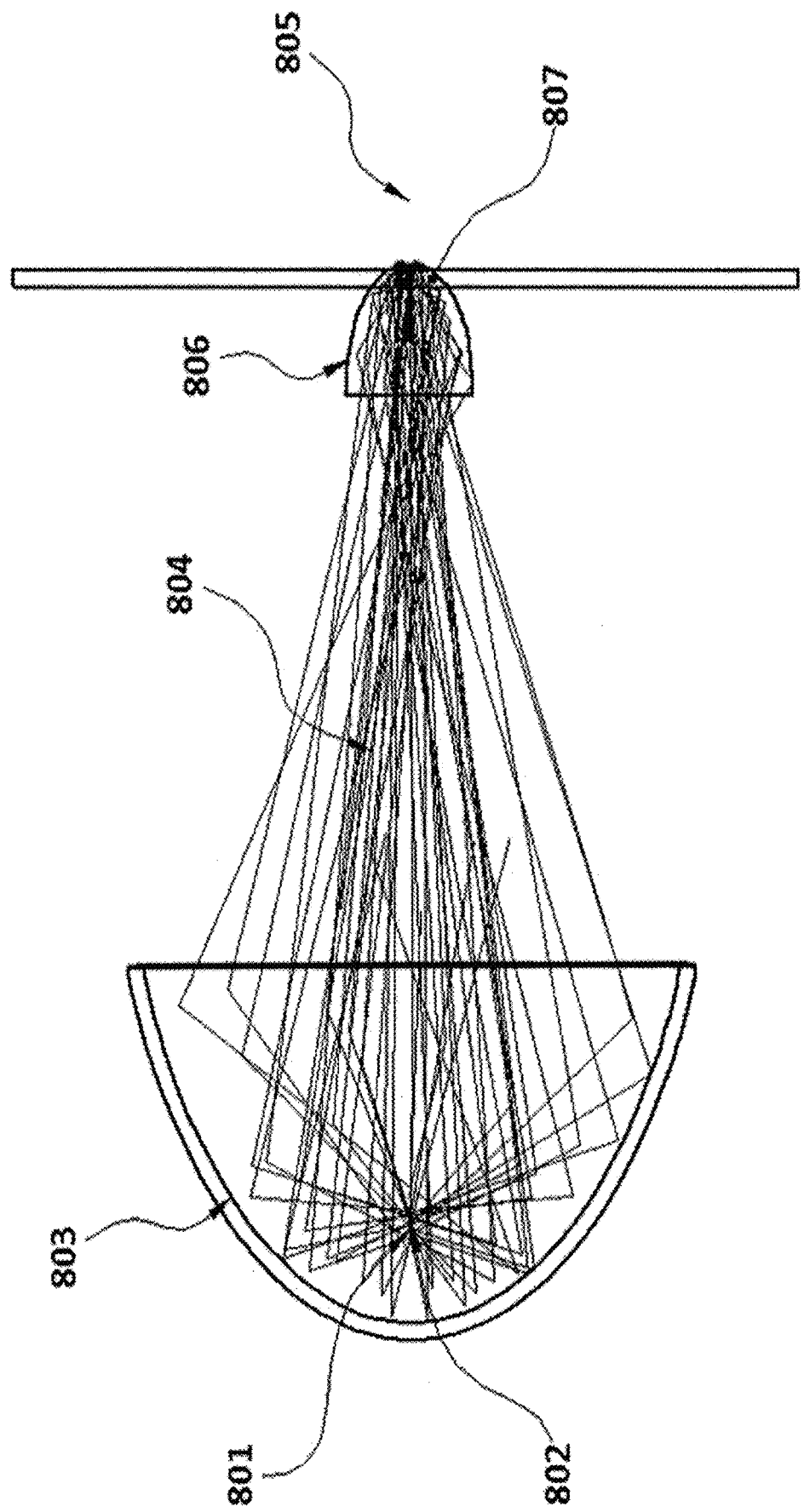
FIG. 8 shows a non-imaging collection optics scheme, according to various embodiments. Illustrated are: lamp arc source or plasma (801), first focal point of the ellipsoidal primary reflector (802), the primary reflector (803), light rays reflected by the primary reflector (804), second focal point of the primary reflector (805), a compound elliptical concentrator (806), and capillary photolysis cell (807).

In some embodiments, illustrated in FIG. 8, an arc lamp source ("source") (801) is positioned on the axis of and nominally at a first focal point (802) of an ellipsoidal primary reflector ("primary reflector") (803). Because of the finite size of the source, it is not possible to place the entire source at the focal point of the primary reflector (as the focal point itself is infinitely small), so most of the light emitted from the source will be emitted from locations which are proximal to, but not precisely at the focal point of the primary reflector.

Figure 9:
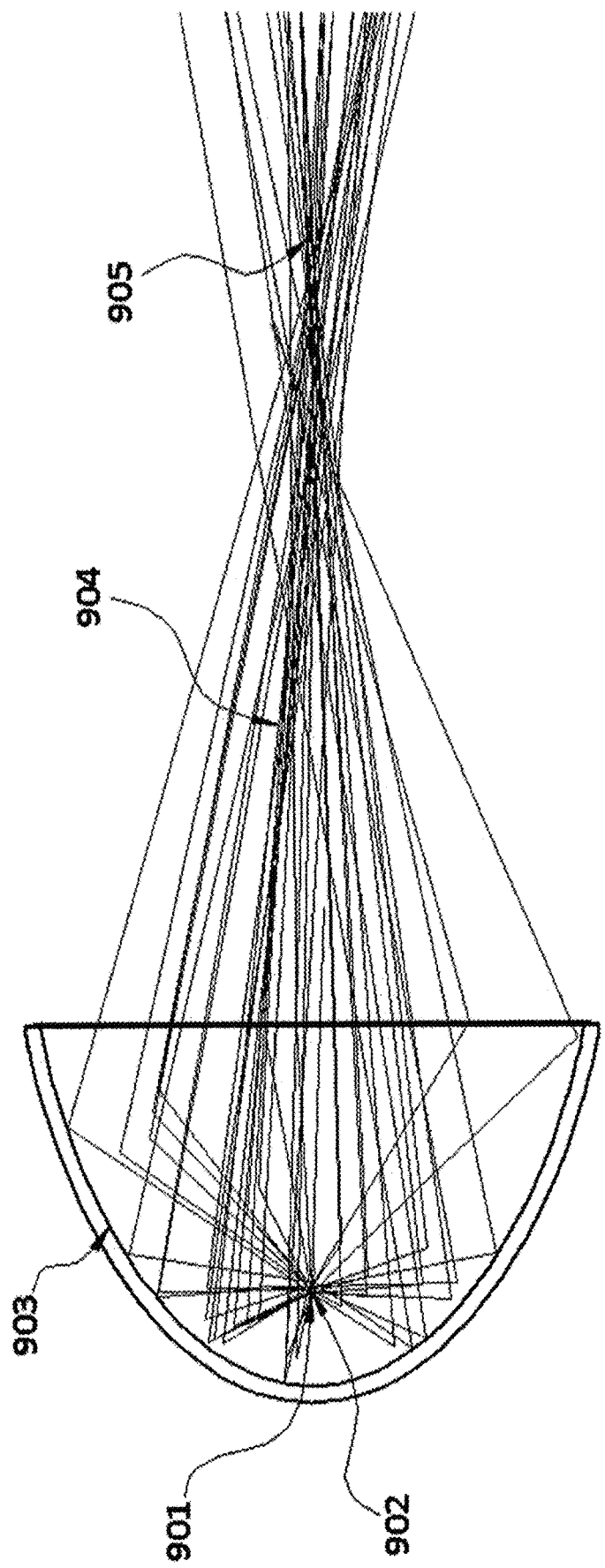
FIG. 9 illustrates portions of a non-focusing collection optics scheme, according to various embodiments. Shown are flash lamp arc (901), first focal point (902), primary reflector (903), light rays (904), and second focal point (905).

Light rays (804) emitted from the source are focused by the primary reflector (an imaging optic) toward a second focal point (805) of the primary reflector, located on the axis of the primary reflector and at a distance from the first focus determined by the particular parameters of the shape of the primary reflector. As is illustrated in FIG. 9, which depicts only the source (901), the primary reflector (903), the first focal point (902), the second focal point (905), and light rays (904), said focused light, were it to proceed to the second focus, would form an imperfect, aberrated image of the source generally at and proximate to the second focus. Limitations on the ability of the primary reflector to form a stigmatic image of the source can be attributed to the finite size of the source, as described above, imperfections in the manufacture of the primary reflector, misalignment of the primary reflector with respect to the source, or other causes well known to those practiced in the art. The photolysis cell, a small volume, if placed at the second focus of the primary reflector or at any location proximate to the second focus where the light intensity is greatest would therefore be illuminated only by a fraction of the light focused by the primary reflector. It is therefore sometimes desirable to employ a secondary optic to further collect the focused light and direct the light to the photolysis cell.

In the described embodiment, illustrated in FIG. 8, a compound elliptical concentrator, or CEC, secondary reflector ("secondary reflector") (806) is positioned to collect the light focused by the primary reflector and direct the light into a small target volume. The photolysis cell (807) is positioned such that the light collected by the secondary reflector is directed into the photolysis cell. In the illustrated embodiment, the photolysis cell is shown as a capillary tube, which may, for example, be inserted into the structure of the secondary reflector in order to position it as desired, being an example of one possible embodiment of photolysis cell. In some embodiments, the photolysis cell comprises an opto-fluidic chip. In some embodiments, exiting light from the photolysis cell is redirected back into the cell using any of the previously described means here in.

For a photolysis cell within a capillary tube it is sometimes desirable to direct light incident on the outer surface of said capillary to the capillary tube. Some benefit in this regard is achieved if the refractive index of the capillary is greater than that of the surrounding medium, as would be the case for a silica or glass capillary in air or nitrogen. In such a case light, light rays incident on the surface of the capillary will be bent on transmittance through the capillary wall generally towards the center of the capillary to some degree, i.e. by virtue of Snell's law of refraction. Such ray bending may be enhanced by forming the capillary such that the index of refraction increases toward its center. Such a device may be designed in such a way as to direct substantially all light penetrating the surface of the capillary to its center. Descriptions and discussion of such a device may be found, for instance in Narimanov, E. E. and A. V. Kildishev, *Optical black hole: Broadband omnidirectional light absorber*. Applied Physics Letters, 2009.; and in Kildishev, A. V., L. J. Prokopeva, and E. E. Narimanov, *Cylinder light concentrator and absorber: theoretical description*. Opt Express, 2010.

Metal Oxide Photo-Catalysis to Create OH Radicals From Water

As practiced in the prior art, a limitation of FPOP HOS analysis arises from the requisite inclusion of $H_2O_2$ in sample containing buffers. Upon UV irradiation, $H_2O_2$ is split into OH radicals, which in turn react with the protein of interest. Being the primary source of OH radicals, $H_2O_2$ must be mixed with target protein before photo-induced OH radical attack can commence. Unfortunately, the inclusion of $H_2O_2$ in the protein supporting buffer can create unwanted and artefactual alteration of protein tertiary, quaternary, and associated higher order structure. The presence of $H_2O_2$ can induce Fenton-like chemistry in a variety of proteins, resulting in uncontrolled OH radical formation with subsequent artefactual protein labeling (Watson, C. et al; *Pulsed electron beam water radiolysis for sub-microsecond hydroxyl radical proteinfoot-printing*; Analytical Chemistry; 2009). In other cases, the solvent properties of $H_2O_2$ are sufficiently different from those of nascent aqueous environments as to cause unwanted conformational change among target proteins of interest (Lasch, P. et al.; *Hydrogen peroxide-induced structural alterations of RNAse A*; The Journal of Biological Chemistry; 2001). As such, prior art requires a limited exposure time to $H_2O_2$ in order to preserve nascent HOS, a requirement that is at odds with the market desire to queue up large numbers of samples in micro-titer plates and perform processing in an automated fashion.

In a simple embodiment, $H_2O_2$ artifacts are avoided by minimizing protein residence time in a microplate prior to sample processing. In some applications, it has been determined that maximum time for $H_2O_2$ exposure should not exceed 30 minutes, when using a 100 mM aqueous solution as is customarily used in the prior art. The typical duty cycle for an automated flash photolysis system will complete the processing of a single sample in about 30-60 seconds. Considering the above noted 30 minute limit, an automated device could only process about 30-60 wells of a 96-well or 384-well microplate before risking the creation of HOS artefacts. In some embodiments, $H_2O_2$ could be mixed with protein buffer using an in-line microfluidic mixer just prior to flash photolysis. While this approach appreciably extends micro-plate residence time, it substantially complicates the system's fluidic circuitry and puts the in-line sample stream at risk of uncontrolled bubble formation arising from the out-gassing of dissolved atmospheric gas as precipitated by the enthalpy of mixing.

Figure 10:
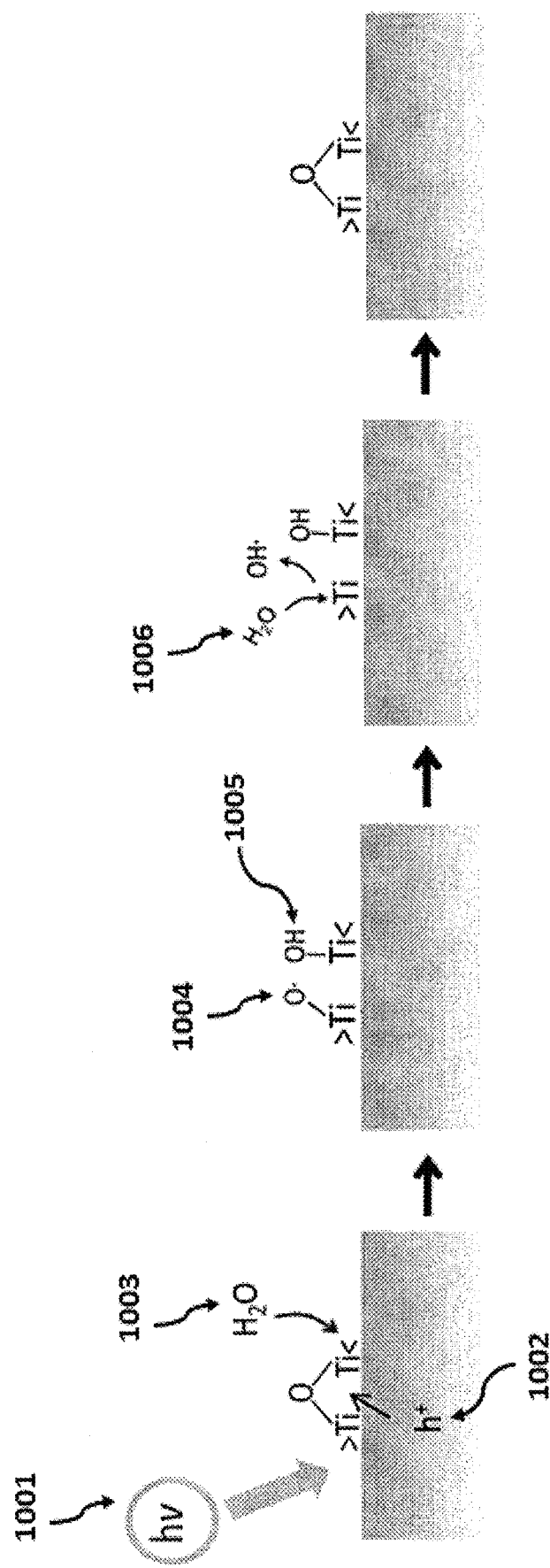
FIG. 10 is an illustration that depicts the photo-catalyzed radical reaction mechanism of $TiO_2$ with adsorbed water, according to various embodiments. Shown are: incident UV or visible radiation hv (1001), electron—hole pair $h^+$ (1002), first adsorbed water molecule (1003), adsorbed superoxide radical (1004), adsorbed OH radical (1005), and second adsorbed water molecule (1006).

Metal oxide photo-catalysts have been used in a variety of applications, many of which are directed towards the decomposition of aqueous pollutants or to lend bactericidal properties to surfaces (Katayama et. al; *Lifetime* and *diffusion coefficient of active oxygen* species *generated in TiO2 sol solutions*; Physical Chemistry Chemical Physics; 2009). In general, such photocatalytic reactions start with the photo-excitation (1001) of electrons and holes ($h^+$) (1002) by irradiation of ultraviolet light as shown in FIG. 10, which depicts the photo-chemically induced catalytic creation of OH radical from water adsorbed to the surface of $TiO_2$. As shown, an intermediate state splits adsorbed water (1003) into adsorbed superoxide anion (1004) and hydroxyl radical (1005), both of which are ultimately released by the subsequent adsorption of water (1006), thus regenerating the photocatalytic surface. During the course of the ensuing chain reaction, much of the liberated superoxide radical is ultimately converted to OH radical, making OH radical the predominant end product. The photo-catalyzed free radical chain reaction persists as long as the metal oxide electron-hole pairs are photo-excited, and decays rapidly then-after.

It is believed that the use of $TiO_2$ and other photocatalytic oxides, such as $WO_3$, $BiVO_4$, $Ta_2O_3$, $ZrO_3$ and/or the like, for FPOP analysis has been previously unexplored. Unlike, $H_2O_2$, metal oxide catalysts do not perturb protein HOS and can be mixed with proteins without concern. Since metal oxide catalysts promote the creation of OH radicals from water at 55 mole/liter concentration, which is 550 times greater than the concentration of 100 mM aq. $H_2O_2$, they promote a comparatively high yield of OH radicals and are completely compatible with many protein buffer systems, such as the large variety of phosphate buffers often used to emulate protein physiological conditions. Finally, because the electron-hole pair reaction period is photo-excitation limited, the duration for OH radical generation closely mirrors the pulse-width of irradiating light, producing an effective OH radical half-life that is consistent with fundamental FPOP requirements.

Figure 11:
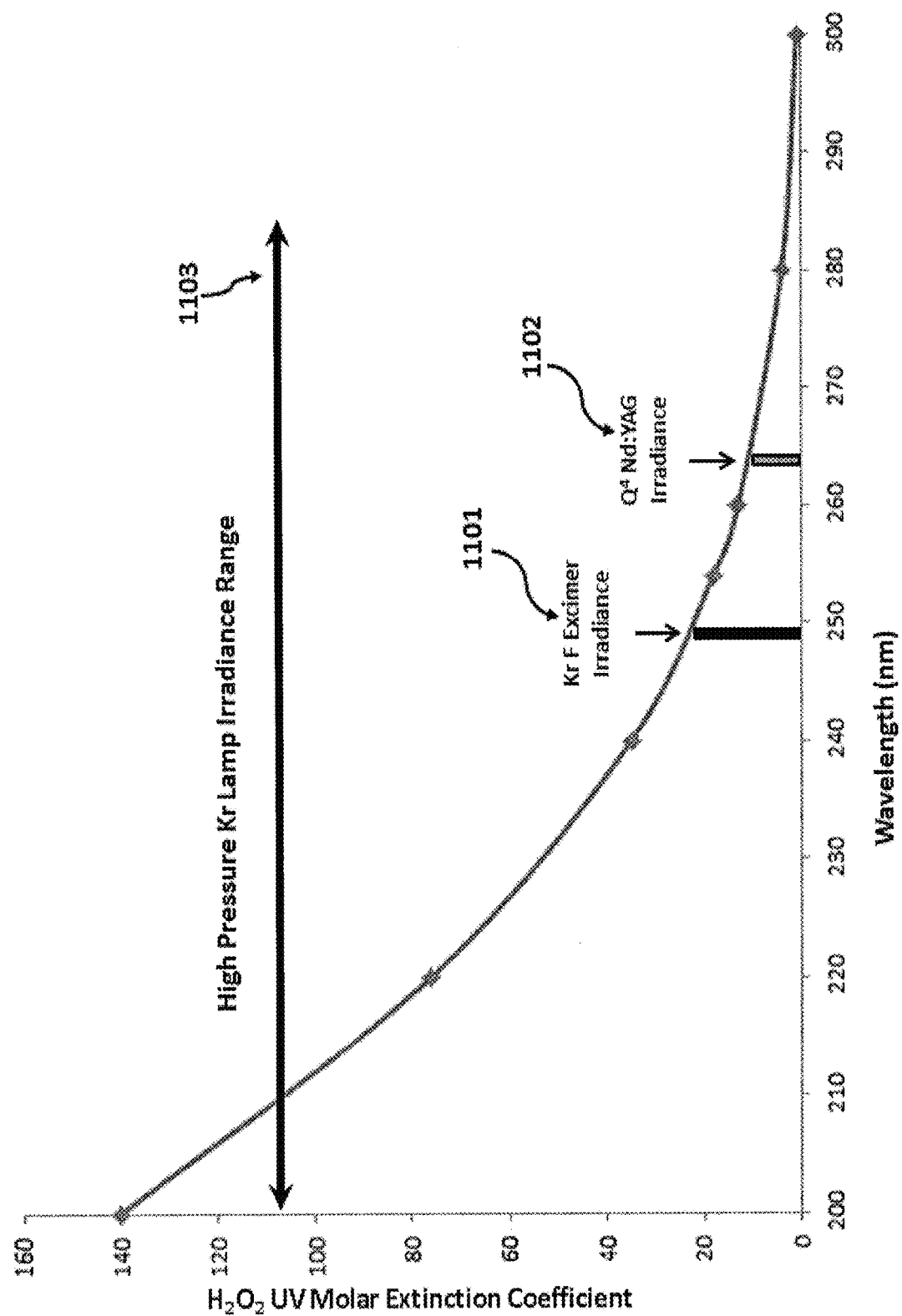
FIG. 11 illustrates the UV absorbance spectrum of $H_2O_2$, according to various embodiments. Shown are the Kr F Excimer laser irradiance wavelength domain and associated $H_2O_2$ absorbance (1101) and frequency quadrupled; neodymium yttrium aluminum garnet laser wavelength domain and associated $H_2O_2$ absorbance (1102); and high pressure krypton lamp spectral irradiance domain (1103).
Figure 12:
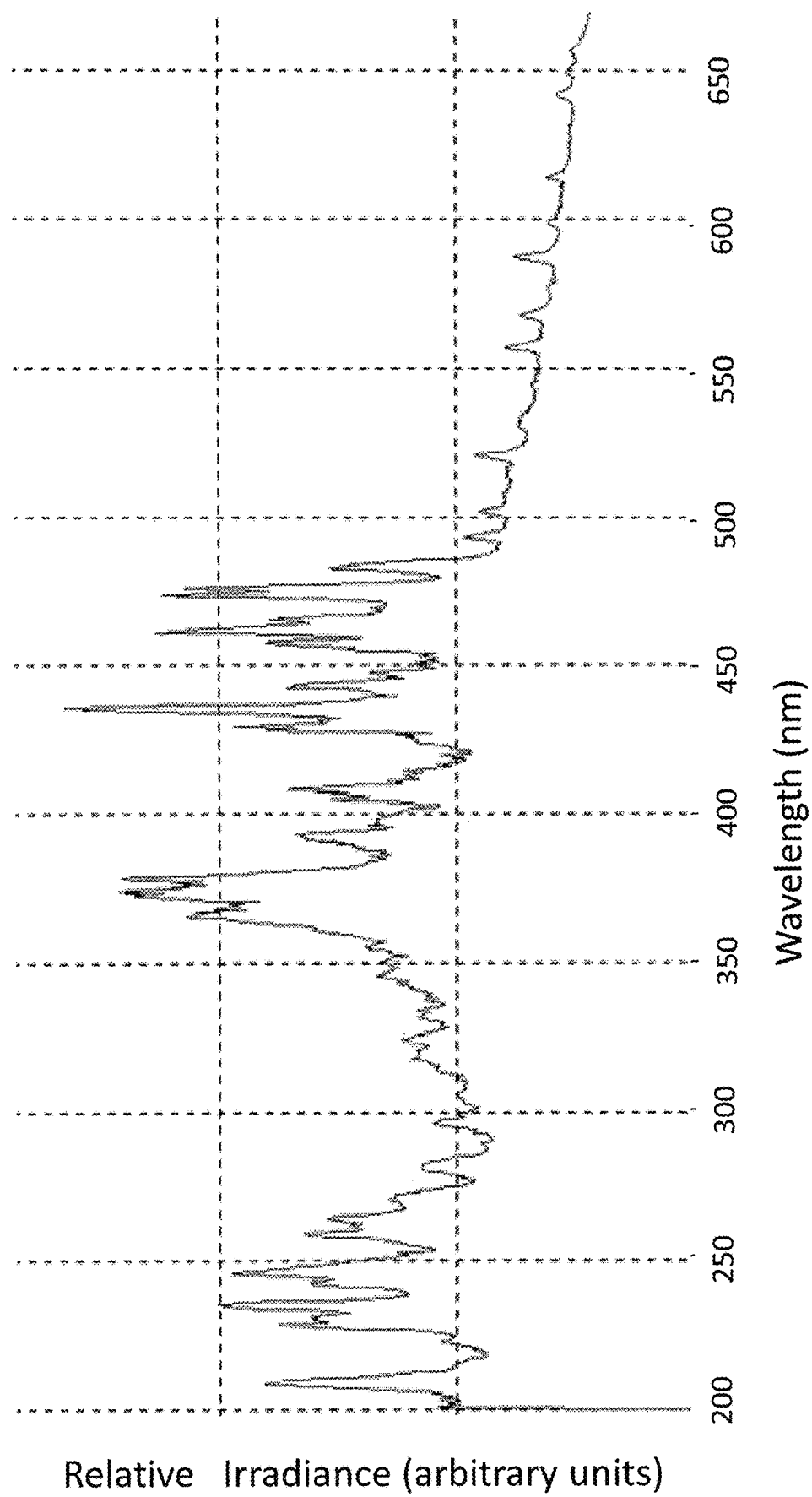
FIG. 12 depicts the output spectrum for a high pressure Kr lamp as measured in the inventor's laboratory.

The UV absorbance spectrum of $H_2O_2$ is depicted in FIG. 11. As can be seen, $H_2O_2$ UV absorbance is substantially higher at 200 nm than it is for the primary wavelengths of a Kr F excimer laser (1101) or frequency quadrupled neodymium yttrium aluminum garnet (Q4 Nd; YAG) laser (1102) as typically employed in the prior art. Also shown is the spectral irradiance range of a high-pressure Kr lamp (1103). FIG. 12 displays the output spectrum of a high-pressure Kr lamp. As can be seen, appreciable spectral irradiance persists ranging from 200 nm to 650 nm. When contrasted to the previously described excimer or Nd:YAG lasers, the Kr lamp output profile substantially overlaps with the "high absorbing" UV wavelength domain of $H_2O_2$. While the short UV wavelength irradiance of a Kr source can create superior levels of OH radical from aqueous $H_2O_2$, unfortunately this short UV spectral band also overlaps with nascent absorbance maxima of many proteins, creating the possibility for unwanted photochemical attack. The same concern applies for the combined use of a Kr source with a metal oxide photo catalyst.

Figure 13:
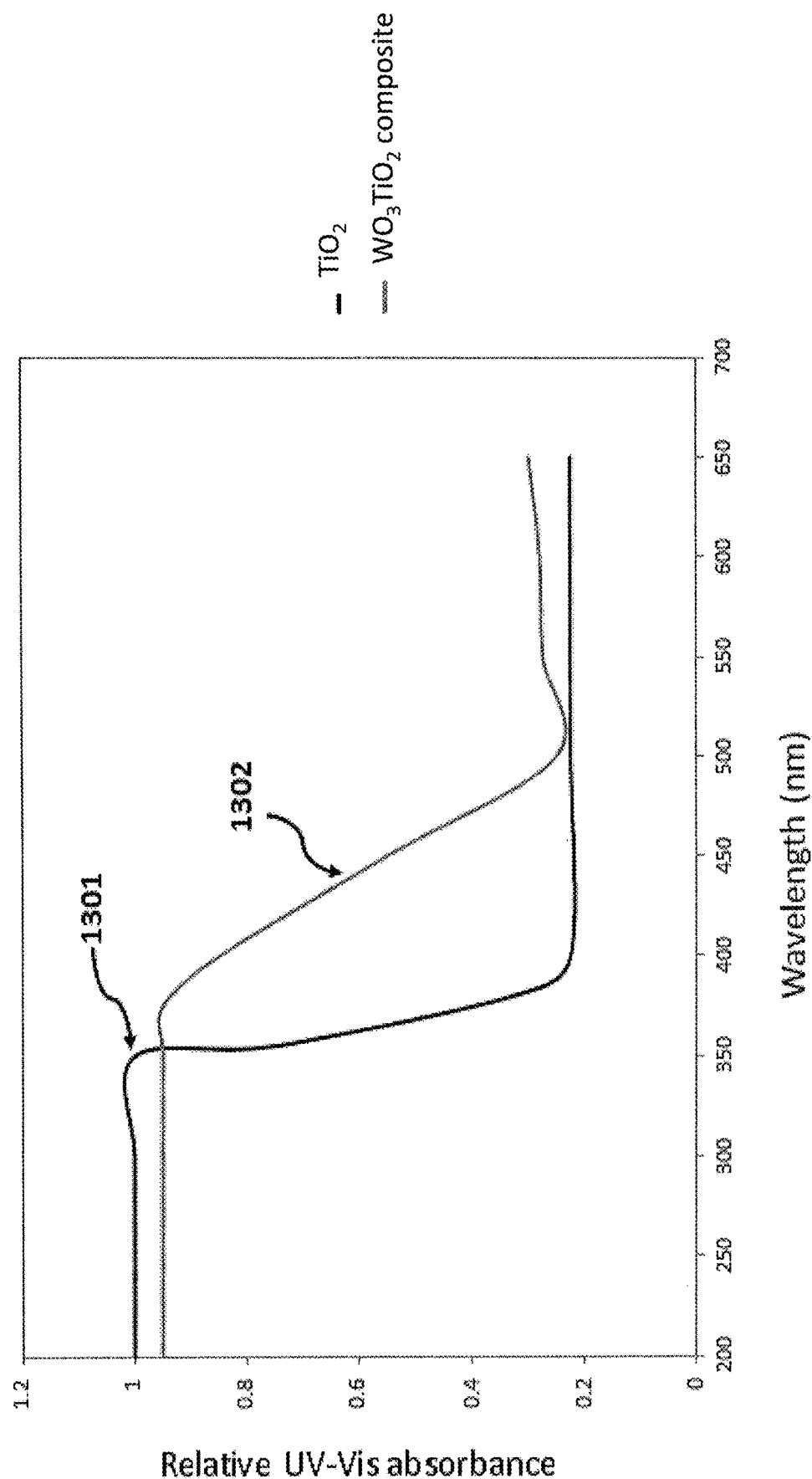
FIG. 13 illustrates the ultraviolet—visible spectrum absorbance properties of two different photo-catalytic metal oxides: $TiO_2$ (1301) and $WO_3TiO_2$ (1302).

FIG. 13 illustrates the measured relative absorbance of two metal oxide catalysts as reproduced from the work of Leskela et al. (Leskela, M et al; *Photocatalytic properties of $WO_3/TiO_2$ core/shell nanofibers prepared by electrospinning and atomic layer deposition*; Chemical Vapor Deposition, 2013). The UV-Vis absorbance profile for $TiO_2$ (1301) is compared to that for a composite oxide of $WO_3$ and $TiO_2$ (1302). As noted the $WO_3/TiO_2$ composite photo-absorbance domain extends out into the visible spectrum, with good over-lap to the Kr lamp output spectrum depicted in FIG. 12. As such, $WO_3/TiO_2$ may represent an improvement over $TiO_2$. Moreover, as considerable absorbance is maintained at wavelengths beyond 280 nm, it is possible to employ a long pass filter in combination with the Kr lamp using a clear fused quartz envelope to mitigate unwanted generation of ozone as well as deleterious photochemical reactions with the protein of interest. The latter can be accomplished by constructing the photolysis cell out of appropriate optical quality material such as BK-7 or Borofloat® glass, which effectively function as a high pass optical filter, optimally transmitting light above 300 nm.

Various embodiments of the invention make use of metal oxide photocatalytic surfaces to generate OH radicals from the water present within aqueous buffers in the process of FPOP HOS analysis. In some embodiments, metal oxides comprise nanoparticles, ranging from but not limited to 0.5-20 nanometers in diameter, that are premixed with sample buffers and introduced into a flash photolysis system. After photo-oxidation, product is collected and the nanoparticles are removed by using preparative separation schemes such as, but not limited to, ultracentrifugation that creates a pellet of nanoparticles and a supernatant of labeled protein. In some embodiments, nanoparticles are immobilized to at least one sample contacting surface of the photolysis cell using covalent attachment means such as, but not limited to, silane linkage. In some embodiments, metal oxide films are deposited upon at least one surface of the photolysis cell using a variety of coating processes which include but are not limited to: dip coating, spin coating, sputter-deposition, electron beam evaporation, vacuum thermal-sublimation, atomic layer deposition, and/or the like. In some embodiments, metal oxide photo-catalysis is used in combination with laser light source such as but not limited to an excimer laser, Nd:YAG laser or pulsed diode laser of appropriate irradiance and wavelength. In some embodiments metal oxide photo-catalysis is used in combination with a flash photolysis system that employs suitable flash lamp embodiments as described herein. In some embodiments, metal oxide photo-catalysis is used in combination with a flash lamp oxidation source and photolysis cell comprised of photo-transmissive material that functions as a long pass filter, selectively transmitting light in the wavelength domain above 280 nm. In some embodiments, the photocatalytic material is comprised of $TiO_2$. In some embodiments, the photocatalytic material is comprised of $TiO_2$ that is composed of 80% anatase and 20% rutile crystalline structure. In some embodiments, the metal oxide photocatalytic material is comprised of a composite blend of a plurality of metal oxides such as but not limited to $WO_3$ and $TiO_2$. In all of the above noted embodiments, metal oxide photo-catalysts may provide a functional, and enabling superior embodiment when compared to the prior art, and as such represent a distinctly unique and substantially improved system configured for performing FPOP HOS analysis.

Various described embodiments make reference to a photolysis cell which may be considered to be comprised of a capillary or opto-fluidic chip. FPOP HRPF experiments using $H_2O_2$ have also been performed by irradiating samples located within the wells of a microplate (Aye, T. T. et al, *Nanosecond laser-induced photochemical oxidation method for protein surface mapping with mass spectrometry*. Anal Chem, 2005). Because the automated processing of microplate experiments are also limited by the requisite inclusion of $H_2O_2$, it is clear that some embodiments include a microplate that obviated the requirement for $H_2O_2$. As such, in some embodiments, the present invention comprises a micro-plate with at least on fluid contacting surface coated with a metal oxide photo-catalyst. Said microplates could comprise an array of at least, but not limited to, 96, 384, and 1536 wells. In some embodiments, said microplates comprise an integrated wave-guiding structure enabling individual microwells to be specifically addressed and illuminating specific regions of said wells, mininizing the loss of irradiance via stray light. While for the purpose of disclosure, reference to microplates have been made. As it is readily recognized by those skilled in the art, any sample containing reservoir could be used for the purpose of metaloxide FPOP HRPF analysis, and as such, the present disclosure is not meant to be restrictive in terms of scope.

Flash Photolysis System: Waveguides and Resonance Structures

In other embodiments of the invention, light may be transmitted to the photolysis cell by means of a waveguiding structure, such as an optical fiber or a wave-guiding structure integrated with the photolysis cell into a single optical component. Said optical component may additionally incorporate fluidic channels for transporting the sample fluid to and from the photolysis cell. The wave-guiding transmission medium may be air or glass or fluid (such as for example the sample fluid) or any suitable medium that will support optical guided modes over the wavelength range appropriate for FPOP HRPF within the structure of the waveguide. In some embodiments, for example, the guiding medium is fused silica. Light may be conducted from the light source to the photolysis cell by any combination of waveguide and free-space (i.e. non-wave-guided) means. For the wave-guiding and resonance embodiments described herein, the light source can be of any pulsed photonic source such as, but not limited to, flash lamp sources, pulsed laser sources, and optically chopped continuous wave light sources, including but not limited to high pressure gas plasma lamps and lasers and or the like.

Wave-guiding structures function to direct light to highly specific regions within a photolysis cell, directing the predominance of said light to only the regions of the photolysis cell in which photo-radical reactions are intended to take place. In this manner, wave-guiding structures are included in some embodiments, and light is specifically directed only to the photo-radical reactive domains of the photolysis cell, avoiding unwanted distribution of light (or stray light) to regions that do not contribute to analyte oxidation. Minimizing stray light off-loads light source irradiance requirements, enabling the use of lower flash energies with associated benefits of reducing unwanted electronic emissions and extending overall lamp life. As described herein, one such embodiment comprises the combination of a wave-guiding structure and immobilized metal oxide photo-catalyst, in which light is specifically transmitted and directed into the photo-catalyst for subsequent photo-induced oxidation reactions.

In some embodiments, light collected as illustrated in FIG. 8 instead of being directed immediately to a photolysis cell, is coupled to a flexible fiber-optic cable, for instance, by any suitable commercially available optical fiber light coupling apparatus. Said light, after passing through to the other end of the optical fiber, is then coupled into the photolysis cell through a second suitable coupling apparatus. Such fiber-optic transmission link may be employed, for instance, for the convenience of arranging componentry in an efficient ordering, or to improve alignment stability.

An integrated optical or opto-fluidic component ("IOC") may be included in an embodiment of this invention and may incorporate structures and functionality of: light source; fluidic flow channels; photolysis cells; optical waveguides; optical coupling apparatus; and fluidic coupling apparatus in any form or combination pursuant to the purposes of providing a photolysis cell; providing means to illuminate said photolysis cell with light; and providing means to introduce a sample fluid into the photolysis cell and subsequently remove said sample fluid such as for subsequent analysis. In some embodiments of a photolysis cell, a photocatalytic substance, for example titanium dioxide ($TiO_2$), is immobilized within or on at least one surface of the photolysis cell. In these embodiments, photo-catalysis occurs at the irradiated surface of the photolysis cell. In some embodiments, a photocatalytic substance is suspended within the sample fluid and is transported with the fluid to the photolysis cell. In these embodiments, photo-catalysis occurs within the irradiated volume of the photolysis cell.

Figure 14:
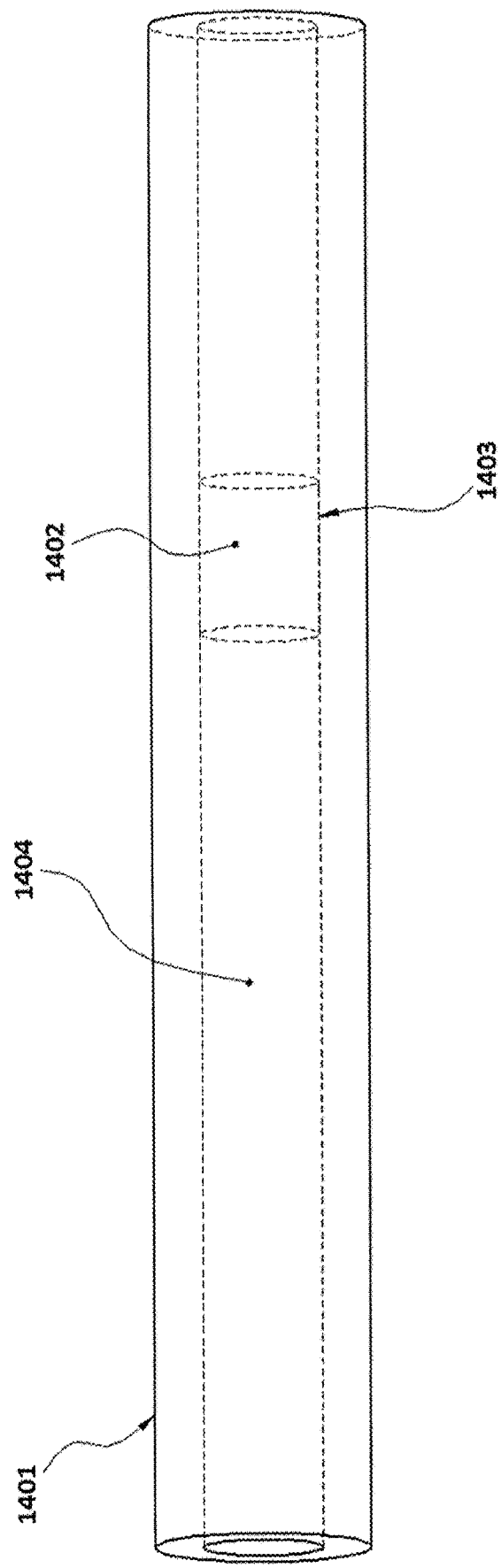
FIG. 14 depicts an integrated opto-fluidic component (IOC) in capillary format, according to various embodiments. Illustrated are: a capillary tube (1401), a capillary photolysis cell (1402) a coat of photo-catalytic material (1403) and sample fluid (1404).

In some embodiments of IOC, illustrated in FIG. 14, the IOC incorporates a capillary tube (1401) wherein the illumination light may be guided to a photolysis cell (1402), said photolysis cell comprising a region within the capillary tube coated on its inner surface with a photocatalytic material (1403) such as $TiO_2$. In this embodiment, the illuminating light propagates along the capillary tube flow cell containing a sample fluid (1404), substantially un-attenuated up to the region coated with the photo-catalyst, initiating the photolysis reaction. In one embodiment, light is guided within the fluid channel of the capillary. In some embodiments, light is guided within the material of the capillary, said material being substantially transparent to light over a wavelength band useful for the photocatalytic reaction. In these embodiments, light is conducted within the capillary material and is coupled into the photo-catalyst coated onto the interior surface of the capillary, initiating the photolysis reaction. Here, coupling of light into the photolysis cell from the waveguide may be by, for example, evanescent coupling, a grating coupler, a prism coupler, a capillary taper, or any appropriate device, as would be understood by one fluent in the art of photonics. Coupling of light into the capillary might be accomplished by any device known in the art.

Figure 15:
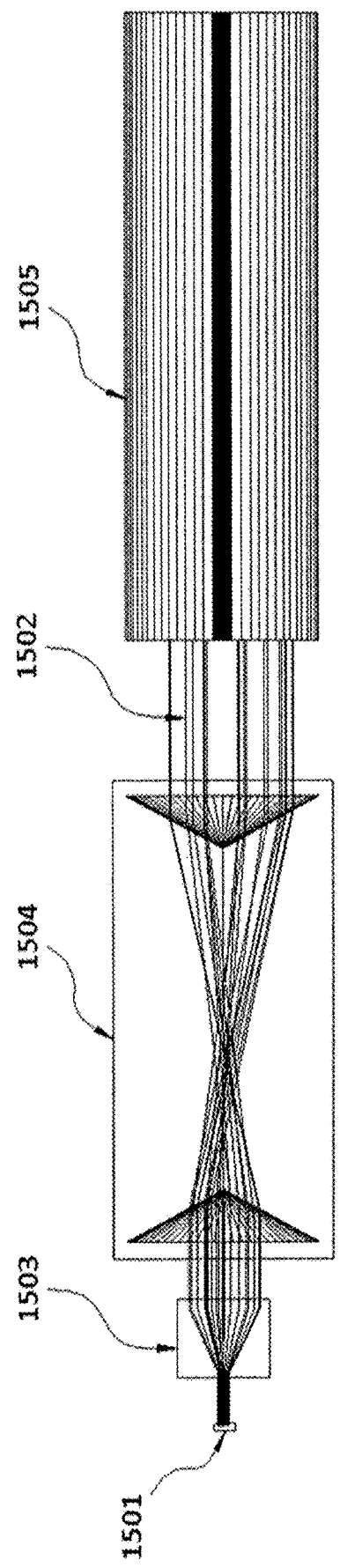
FIG. 15 depicts a light coupling system for a capillary IOC, according to various embodiments. Shown are: a light source (1501), light from said source (1502), an optical beam expander (1503), an axicon assembly (1504) and capillary (1505).
Figure 16:
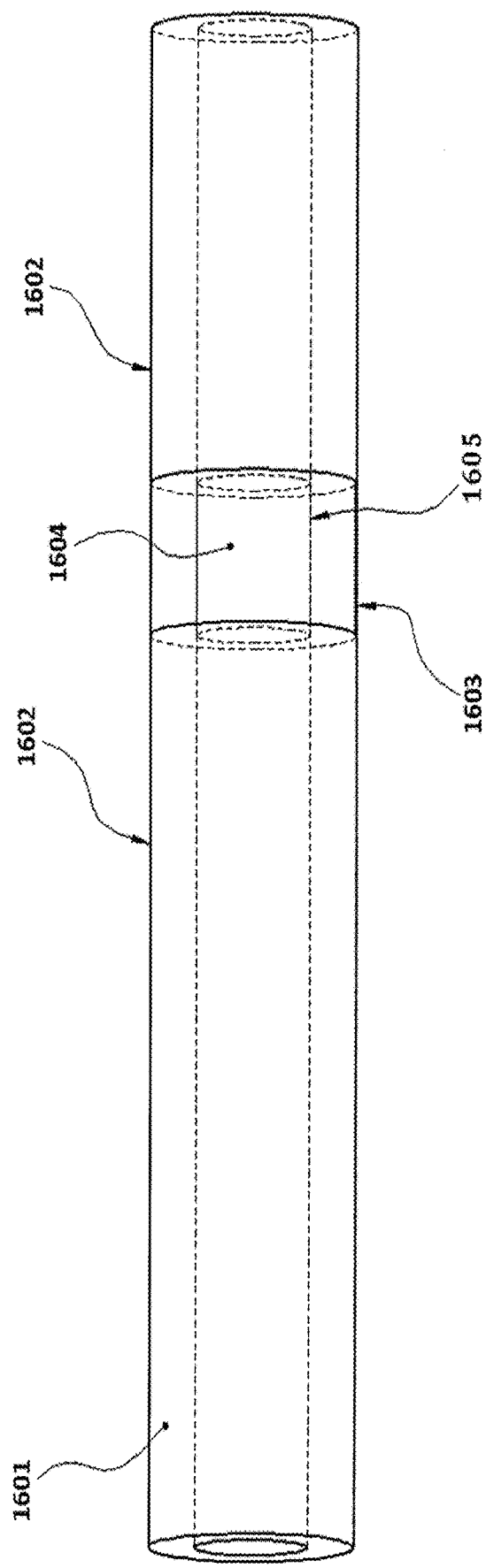
FIG. 16 illustrates a capillary OC with integrated waveguiding structure, according to various embodiments. Depicted are: a capillary tube (1601), capillary tube guiding mode material (1602), a capillary section without guiding mode material (1603), a photolysis cell (1604) and photo-catalytic material (1605).

In some embodiments, illustrated in FIG. 15, a source (1501) of light (1502) is coupled through a beam expander (1503) and an axicon assembly (1504) into the material of the capillary (1505). The axicon assembly is arranged to produce a ring of light of size and character suitable for coupling into the capillary material. In some embodiments of IOC, illustrated in FIG. 16, the IOC incorporates a capillary tube (1601) with one or more sections that support guided modes within the material of the capillary (1602), and with a section that does not substantially support guided modes (1603). In this embodiment, the photolysis cell (1604) comprises the capillary tube of that section of the capillary that does not support guided modes in the material of the capillary, such that light leaks into the capillary tube, and said capillary section is coated on its inner surface with a photocatalytic material (1605) such as $TiO_2$. Here, coupling of light into the photolysis cell from the waveguide may be by, for example, evanescent coupling, a grating coupler, a prism coupler, or any appropriate systems as would be understood by one knowledgeable in the art of photonics.

Figure 17:
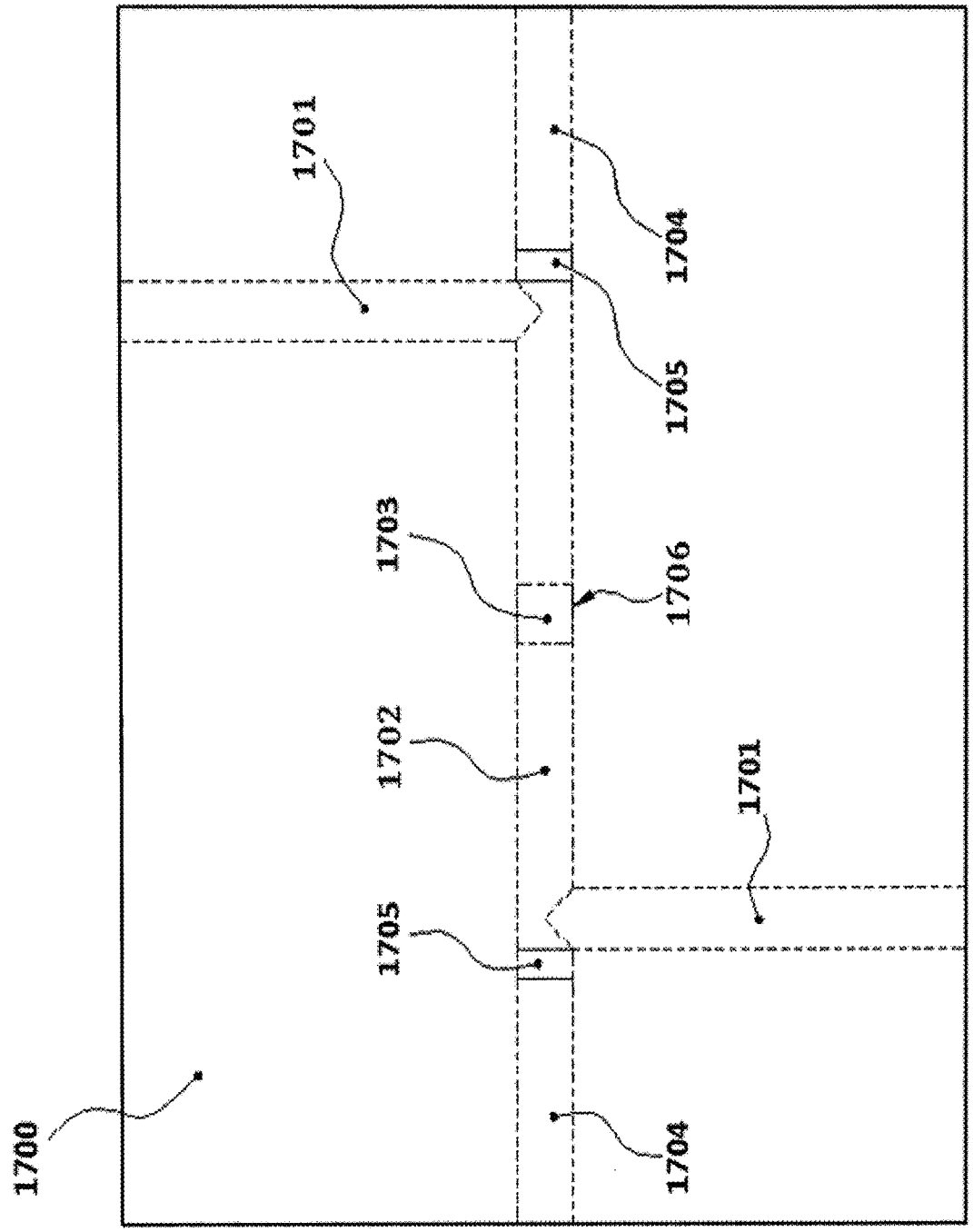
FIG. 17 illustrates an IOC fluidic chip, according to various embodiments. Depicted are: IOC (1700), microfluidic channels (1701), optical wave guide (1702), photolysis cell (1703), input and output waveguides (1704), optical—fluidic coupling structure (1705) and photo-catalyst coating (1706).

In another embodiment, illustrated schematically in FIG. 17, the IOC (1700) is an integrated opto-fluidic chip incorporating one or more fluidic channels (1701) for the introduction and removal of the sample fluid, at least one of which said fluidic channels supports waveguide modes (1702) and contains a photolysis cell (1703); one or more waveguides (1704) for the introduction of light to and extraction of light from the photolysis cell; and associated structures for coupling of light into and out of the fluid (1705). The photolysis cell may also contain a photo-catalyst (1706). In this embodiment, light may be conducted into a fluidic channel and be guided within the fluidic channel to a photolysis cell. Additionally, a source of light for performing radical dosimetry may be introduced in the same fashion, being conducted to and from the photolysis cell by these same systems, and being introduced to the IOC, for example, through one waveguide and extracted through another.

Figure 18:
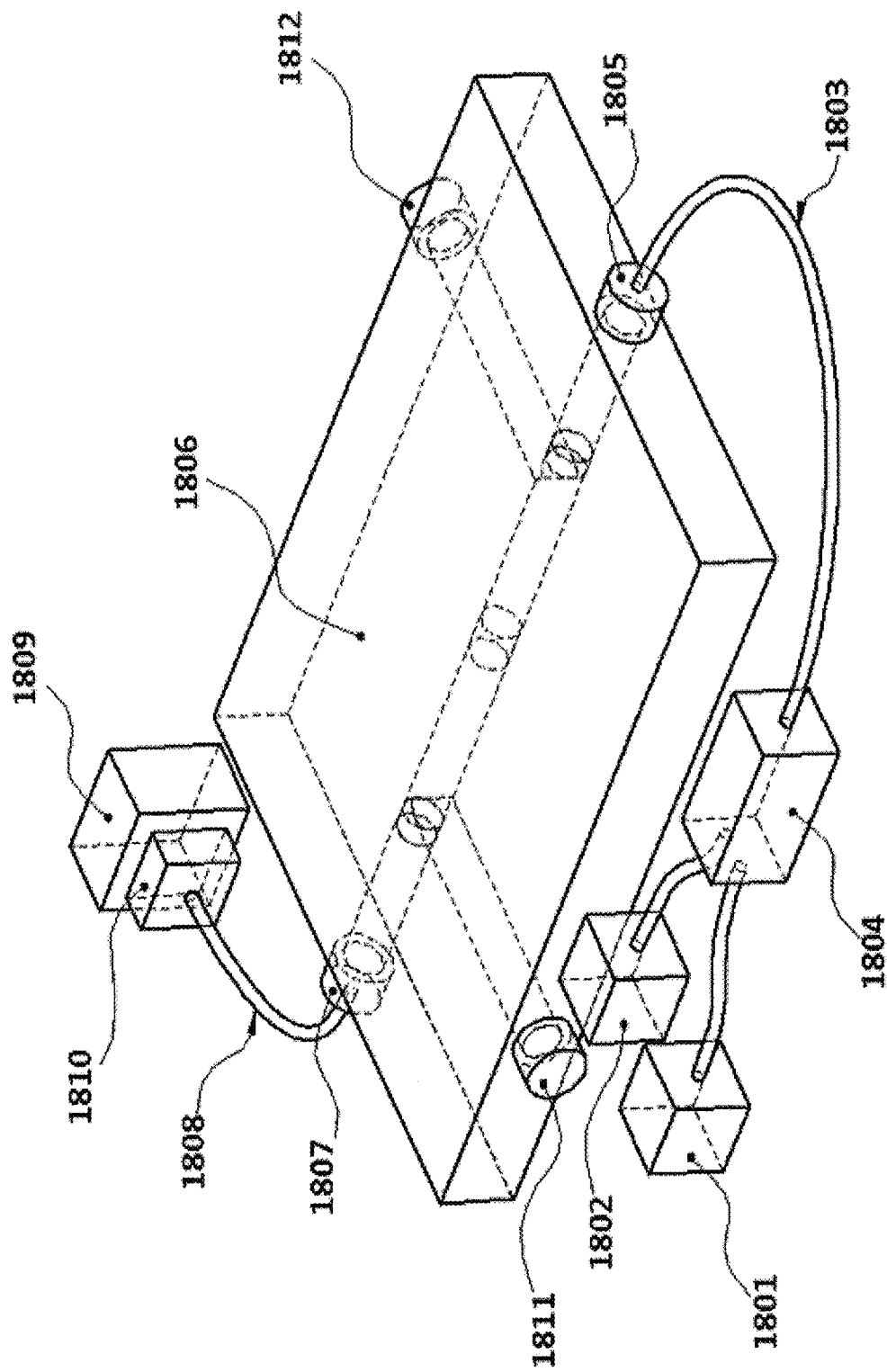
FIG. 18 illustrates the integration of an IOC with a flash photolysis system and radical dosimeter system, according to various embodiments. Shown are: photolysis pump source (1801), dosimeter probe source (1802), input optical fiber (1803), optical coupler (1804), fiber—IOC optical coupler (1805), IOC (1806), IOC output optical coupler (1807), output optical fiber (1808), photo detection apparatus (1809), shutter assembly (1810), input fluidic channel port (1811) and output fluidic channel port (1812).

A schematic illustrating some embodiments of an opto-fluidic system employing such an optical chip IOC (1806) for flash photolysis is shown in FIG. 18, with reference to FIG. 17. Here a photolysis light source (1801) and a radical dosimetry light source (1802) are coupled into an input optical fiber (1803) by means of an optical coupler (1804)

that combines the two light sources into the input optical fiber. The input optical fiber in turn is optically coupled through a second optical coupler (1805) to the IOC (1806), and is conducted to the photolysis cell as described above (and illustrated in FIG. 17), within which the photolysis reaction takes place. Light from the radical dosimetry light source is conducted to the photolysis cell by the same described means and additionally extracted from the IOC through a third optical coupler (1807) into an output optical fiber (1808). Light is conducted by the output optical fiber to a photo-detection apparatus (1809), which may contain a shutter (1810) or other device to protect the photodetector from the light emitted by the photolysis light source. A sample fluid is introduced to the IOC at a fluidic input port by means of an input fluidic connector (1811). Said sample fluid is then conducted through the fluidic channels of the IOC to the photolysis cell, where it may be irradiated by light from the photolysis light source; exposed to hydroxyl radicals generated by a photo-catalyst within the photolysis cell; and irradiated by light from the radical dosimetry light source. The sample fluid is then conducted to a fluidic output port, and extracted through an output fluidic connector (1812).

In some embodiments, light not absorbed within the photolysis cell may be redirected, such as by one or more reflective surfaces, distributed Bragg reflectors, or other devices known in the art, to the photolysis cell for the purpose of, for example, increasing absorption of light within the photolysis cell. Distributed Bragg reflectors are described, for example in Yariv, A. and P. Yeh, *Optical Waves in Crystals: Propagation and Control of Laser Radiation*. Wiley Classics Library. 2002: John Wiley & Sons. 604; and in Yeh, P., *Optical Waves in Layered Media*. 2005: John Wiley & Sons. 416.

The integrated opto-fluidic component may contain one or more resonant structures, which may serve to confine or localize optical fluence or energy. Such a structure may be used, for instance, to enhance the effectiveness of a photo-catalyst exposed to the resonating optical field by exposing said catalyst to a higher optical fluence than might be achieved in the absence of such a resonator. Much literature exists describing resonator waveguide structures for various applications, for example Yalcin, A., et al., *Optical sensing of biomolecules using microring resonators*. IEEE Journal of Selected Topics in Quantum Electronics, 2006. 12(1): p. 148-155; Zullo, R., et al. *Whispering-gallery mode resonator sensors based on liquid droplets. in Laser Resonators, Microresonators, and Beam Control XVIII*. 2016. San Francisco, California, United States: SPIE; Scholten, K., X. Fan, and E. T. Zellers, *Microfabricated optofluidic ring resonator structures*. Appl Phys Lett, 2011.; Fan, X., et al., *Sensitive optical biosensors for unlabeled targets: a review*. Anal Chim Acta, 2008.; and Foreman, M. R., J. D. Swaim, and F. Vollmer, *Whispering gallery mode sensors*. Advances in Optics and Photonics, 2015. Here we optionally apply uniquely modified resonators for the purpose of inducing photolysis as part of a means to perform FPOP HRPF.

In combination with a flash light photolysis source, resonance structures function to effectively localize and somewhat amplify the absorption of photolysis light into intended reactants for photolysis. In this fashion, resonance structures benefit the process of FPOP in a manner akin to wave-guiding structures in so far as they minimize stray light by significantly minimizing loss of photolysis light once the photolysis light has been transmitted to specified regions of the photolysis cell. The resonance phenomenon functions to capture and retain photolysis light in the photolysis cell, and as such light doesn't exit the photolysis cell after an initial pass that irradiates intended analyte, as depicted in FIGS. 6-9.

An example of such a resonant structure is a ring resonator waveguide. A ring resonator waveguide is a waveguide formed in the shape of a loop such that light coupled into the ring resonator will resonate within the loop. Light may then be coupled out of the resonator, for example, into a photolysis cell. One or more ring resonators may be incorporated into an opto-fluidic chip, or formed as a section of a capillary, for example. Design forms of such resonant structures incorporated into this invention allow for a sample fluid to be brought either into contact with the resonant structure or close enough to the resonant structure to allow light energy to be transmitted from the resonant structure into the sample fluid by means such as, for example, evanescent wave coupling. In some embodiments of this invention, a photo-catalyst either flows in the sample fluid or is immobilized on a structure that is both in physical contact with the sample fluid (e.g. by immersion) and close enough to the resonant structure to allow light energy to be transmitted from the resonant structure into the photo-catalyst.

Figure 19:
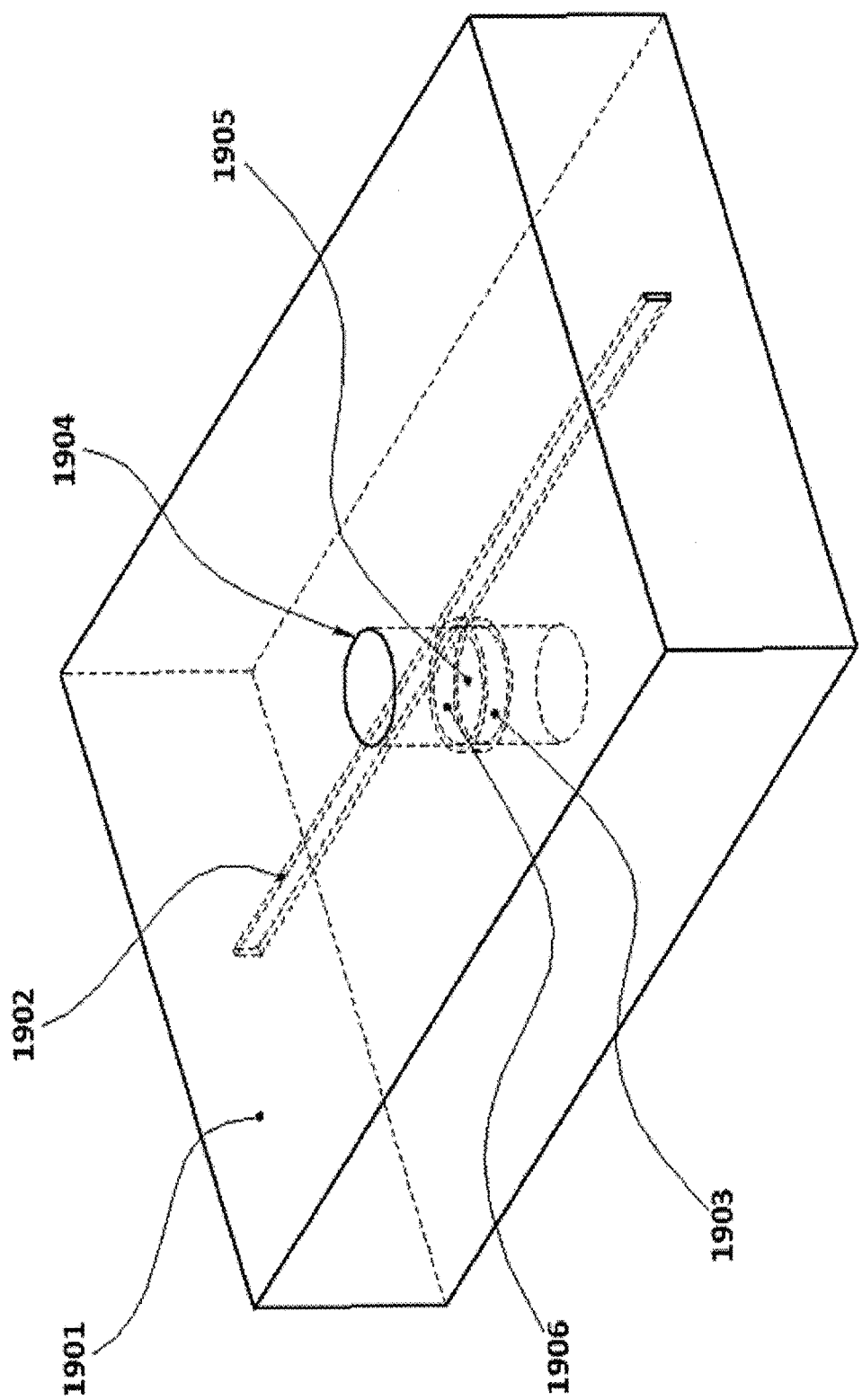
FIG. 19 depicts an IOC with integrated ring resonator, according to various embodiments. Depicted are: IOC (1901), optical wave guide (1902), ring resonator (1903), microfluidic channel (1904), photolysis cell (1905) and photo-catalyst (1906).

Some embodiments of opto-fluidic chip are illustrated schematically in FIG. 19. The chip (1901) contains an optical waveguide (1902); a ring resonator (1903); a fluidic channel (1904), and a photolysis cell (1905). The opto-fluidic chip may also contain a photo-catalyst (1906) immobilized within the photolysis cell. The opto-fluidic chip may also contain apparatus to couple light from the waveguide into the ring resonator and to couple light from the resonator into the photolysis cell. As with the opto-fluidic system embodiment illustrated in FIG. 18, this embodiment of opto-fluidic chip could be used to couple light into and out of the optical waveguide and to couple fluid into and out of the fluidic channel.

Figure 20:
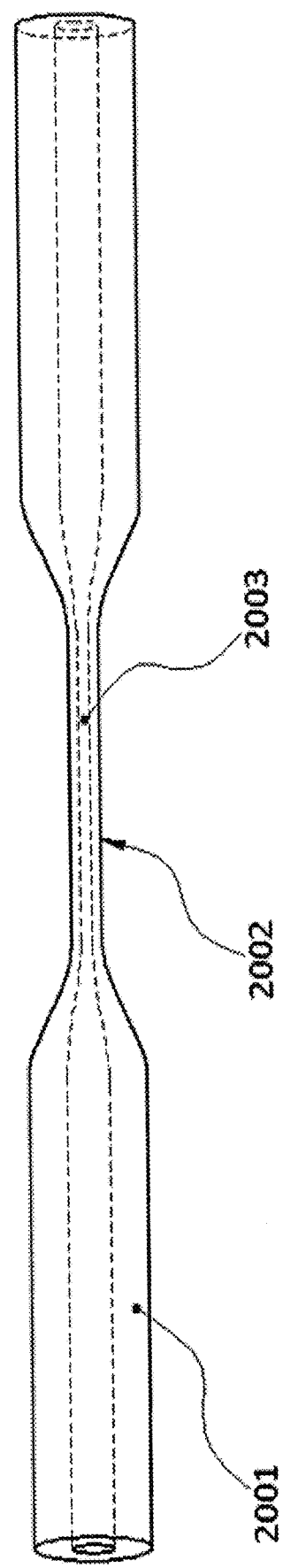
FIG. 20 depicts a capillary optical resonator photolysis cell, according to various embodiments. Shown are: wave-guiding capillary tube (2001), constricted section (2002) and photolysis cell region (2003).

In another embodiment, illustrated in FIG. 20, the optical resonator is formed as apart of a wave-guiding capillary tube (2001) which has a constricted section (2002) within which resonance modes may be sustained. Said constricted section might be formed by, for example, drawing under heat to form a taper, as described in White, I. M., et al., *Label-free detection with the liquid core optical ring resonator sensing platform*. Methods Mol Biol, 2009.; Scholten, K., X. Fan, and E. T. Zellers, *Microfabricated optofluidic ring resonator structures*. Appl Phys Lett, 2011.; and Zamora, V., *Refractometric sensor based on whispering-gallery modes of thin capillaries* Optics Express, 2007., or by etching (Wang, H., et al., *Fiber pigtailed thin wall capillary coupler for excitation of microsphere WGM resonator*. Opt Express, 2013.) or by any suitable means. A photolysis cell (2003), through which the sample fluid flows, is contained within or formed of the constricted section (2002). The photolysis cell may contain a photo-catalyst within the photolysis cell, either flowing with the sample fluid or immobilized within the photolysis cell. Light is conducted from the resonator into the photolysis cell by evanescent wave coupling, by coupling structures fabricated with or onto the capillary tube or by other means known in the art.

Figure 21:
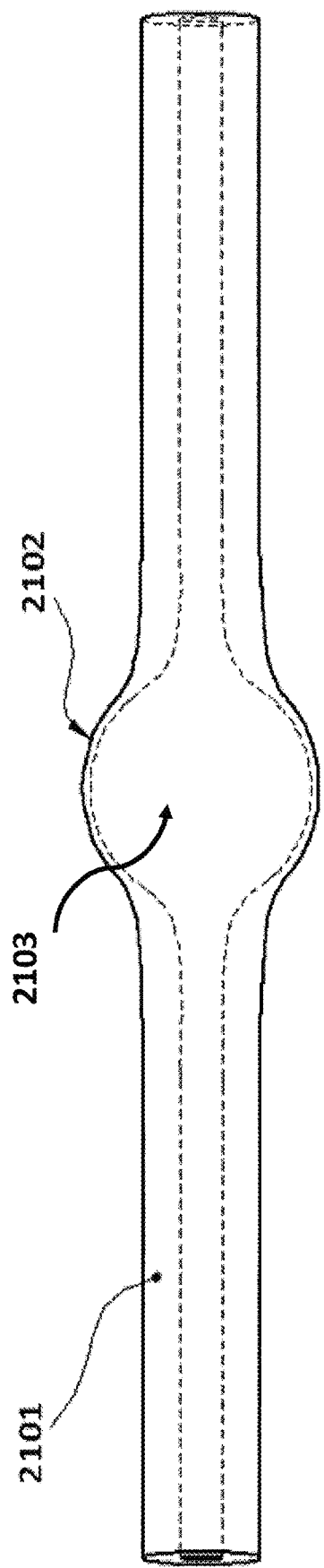
FIG. 21 depicts a capillary micro-bubble optical resonator, according to various embodiments. Shown are the wave-guiding capillary (2101) and microbubble resonator (2102).

In some embodiments, illustrated in FIG. 21, an optical resonator is formed as part of a wave-guiding capillary tube (2101) within which a microbubble resonator (2102) is formed, such as described in Testa, G., G. Persichetti, and R. Bernin, *Optofluidic approaches for enhanced microsensor performances*. Sensors (Basel), 2014. Here, whispering gallery resonance modes are supported within the thinned wall of the microbubble and coupled evanescently into the inner tube of the capillary and leak out into the photolysis cell (2103).

Systems to improve transmission of light from a capillary ring resonator into the capillary tube ("core") have been described, e.g. forming a capillary with refractive index profile that increases towards the core (Zhu, D., et al., *Radially graded index whispering gallery mode resonator for penetration enhancement*. Opt Express, 2012.), shifting modal energy towards the core. This discussion illustrates a few of the many possible approaches that may be used to conduct light to a fluidic photolysis cell; concentrate light into a fluidic photolysis cell; and conduct a sample fluid to and from a photolysis cell. It is intended here to consider any such devices in the execution of FPOP HRPF in various embodiments of this invention.

Closed-Loop Control Radical Dosimetry System

A technical limitation of FPOP HRPF arises from the reaction of OH radicals with background or non-analyte components in the sample, such as buffer constituents and incipient solutes. Variability in the degree of background scavenging causes trial-to-trial irreproducibility, which has limited comparative studies (Niu, B. et al.; *Dosimetry determines the initial OH radical concentration in fast photochemical oxidation of proteins (FPOP)*; Journal of the American Society for Mass Spectrometry; 2015). While OH radicals are excellent probes of protein topography, they also react with many compounds found in analytical preparations. Competition between target protein and background scavengers for free OH radicals exists. As such, to insure reproducible results it is helpful to measure the effective concentration of available radical to oxidize the target protein and to accordingly adjust total radical production.

In photochemistry, effective radical concentration is measured using an internal standard often referred to as a dosimeter internal standard. Ideally, a dosimeter compound would have: a simple relationship between effective radical concentration and dosimeter response; a simple, rapid, and non-destructive measurement means; and be unreactive to most proteins. US patent application publication 2014/0030751 A1 teaches the use of radical dosimetry for the assessment of background scavenging. An approach to determining free OH radical concentration by measuring the absorbance change of adenine, a radical dosimeter internal standard, is described. Adenine competes with the protein sample, as well as with radical scavengers within the buffer, with an established reaction rate, allowing for normalization of radical production to compensate for differences in radical scavenging. Unlike other successful radical dosimeter internal standards that rely upon mass spectrometry measurements, adenine-based radical dosimetry gives accurate measurements using simple UV absorbance (Buxton, G. V., et al., *Critical review of rate constants for the reactions of hydrated elctrons, hydrogen atoms, and hydroxyl radicals in aqueous solution*; J. Phys. Chem. Ref. Data; 1988). The reaction products of adenine with hydroxyl radicals have been well-characterized both experimentally and in high-level theory (Xie, B. et al, *Hydroxyl Radical Dosimetry for High Flux Hydroxyl Radical Protein Footprinting Applications Using a Simple Optical Detection Method*. Anal Chem, 2015.; Naumov, S. et al, *The energetics of rearrangement and water elimination reactions in the radiolysis of the DNA bases in aqueous solution (eaq- and \*OH attack): DFT calculations*. Radiat Res, 2008).

Upon photo-oxidation, adenine loses UV absorbance at 260 nm, and this loss of UV absorbance is linear with effective hydroxyl radical concentration, as altered by changes in generated OH radical or by variance of radical scavengers. The measured absorbance of adenine is also linear with protein and peptide oxidation products across a wide variety of amino acids, and adenine is unreactive under most conditions. As such the variability in measured adenine absorbance change (before and after photo-exposure) can be assessed as a means to monitor changes in background scavenging. Once background scavenging has been assessed, corrections can be applied to compensate for trial to trial variability. In some embodiments, photo-irradiance can be altered proportionally with changes in back-ground scavenging. Irradiance can be increased to compensate for increased levels of scavenging or decreased to address decreased levels of scavenging. In another embodiment, the measured abundance of the oxidized species, as detected by mass spectrometry or some other detection scheme such as but not limited to isoelectric focusing electrophoresis, in two or more different trials could be normalized between runs by multiplying said response by a normalization factor derived from the ratio of adenine absorbance change for the different trials.

In US patent application publication 2014/0030751 A1, an off-line approach to collecting photo-exposed adenine and associated analyte protein is taught, where flow is diverted from a capillary photolysis cell and is directed to an off-line UV detector. The '751 approach consumes substantial product (several microliters) and requires much time to generate sufficient volume to transport the sample and to perform UV absorbance measurements.

The '751 approach teaches the use of high fluence UV lasers to perform FPOP. However, reliable fluence control of high energy UV lasers is difficult to achieve. One approach is by varying the drive voltage of the lasing circuit. However, reducing laser drive energy to levels near or below threshold will result in poor flash-to-flash reproducibility, further exacerbating the irreproducibility of HRPF. As such, high energy laser fluence is typically controlled by using a down-stream, optical attenuator. Attenuation can be achieved using a gradient neutral density filter or Fresnel loss attenuator; however, these approaches have limited life as they become rapidly damaged by laser high energy irradiance that causes ablation of absorbing optical films along with solarization of the underlying substrate. A more reliable, prior art approach to control laser fluence relies upon changing the focused spot size. Spot size is increased to reduce fluence and decreased to increase fluence. While addressing attenuator limited life, changing laser spot size also changes irradiated volume. Changing irradiated volume alters effective OH radical concentration to levels beyond that which is simply attributed to alterations in fluence for a fixed volume. As a spot changes its size, it illuminates a varying amount of sample and buffer housed within the photolysis cell. Since OH radicals will be formed in different volumes of buffer, the net change in free OH radical concentration will be driven by both alterations in fluence and dilution volume, making for a complicated scheme to model and effectively control. As such, some embodiments provide a broad dynamic range of fluence control without altering irradiated volume. Moreover, some embodiments are configured such that closed-loop radical dosimetry can be performed without undue increased consumption of sample or extended sample processing time. Further, some embodiments are configured such that the measured abundance of labeled product can be adjusted in accordance to measured changes in background scavenging, using a post-analysis, data processing approach.

Figure 22:
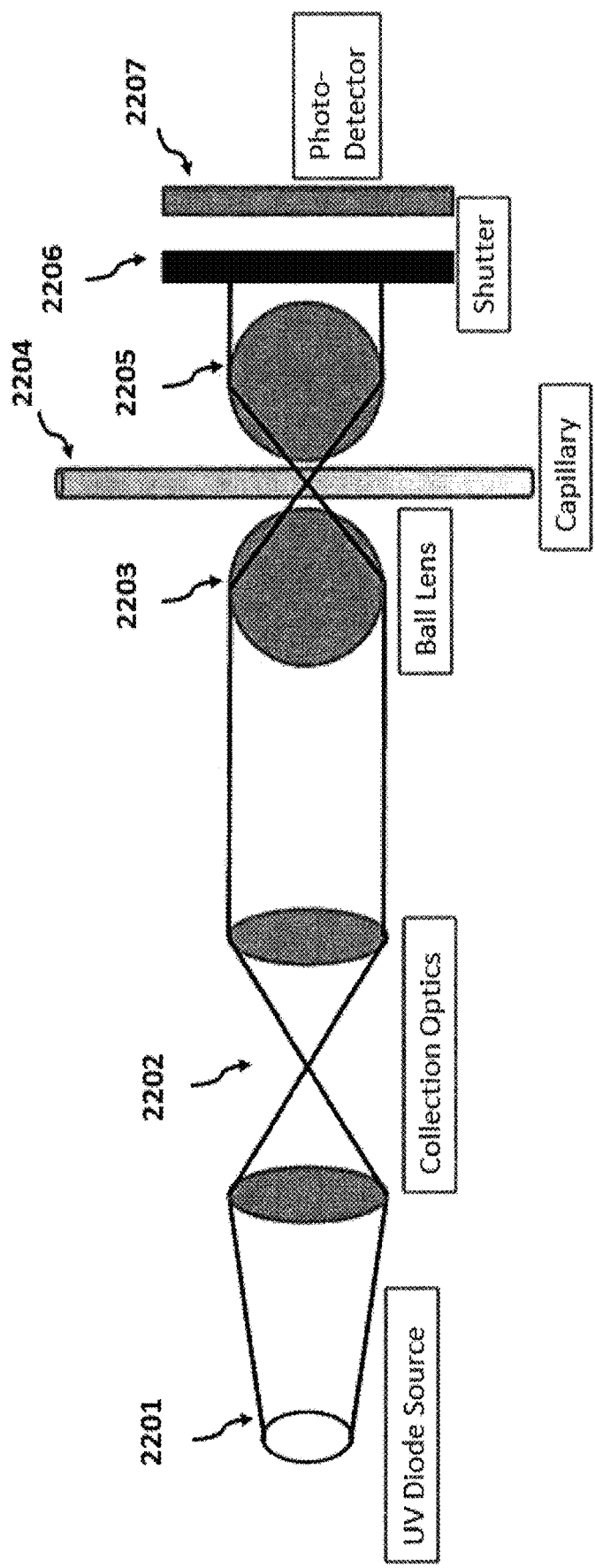
FIG. 22 depicts a free-space propagation radical dosimeter optical bench combined with a capillary photolysis cell, according to various embodiments. Shown are: UV light emitting diode source (2201), collection optics assembly (2202), ball lenses (2203 & 2205), capillary photolysis cell (2204), shutter assembly (2206) and photo detector (2207).

FIG. 22 depicts the optical components an embodiment of a closed loop radical dosimetry system that uses a capillary photolysis cell. In an alternative embodiment, an opto-fluidic (2307) cell is used as a photolysis cell in lieu of a capillary. In FIG. 22, UV probe dosimetry light is provided by a light emitting diode (LED) source (2201). For adenine internal standard radical dosimetry, the LED source may be, but not exclusively comprise, a narrow bandwidth (≤12 nm), 260 nm LED, such as available from QPhotonics (Ann Arbor, MI, USA). Light is collected and collimated by a collection optics assembly (2202). Collimated light is propagated through free space to a UV transparent ball lens (2203). In FIG. 22, the photolysis cell is a fused silica capillary (2204) of properties as further described herein. Light is focused into the capillary and then passes out to a ball lens (2205), which collimates and transmits the exiting light to a shutter assembly (2206). The shutter assembly protects the photodetector elements from photolysis source high intensity light. The shutter is closed during the photolysis source flash and is opened during the internal standard—dosimeter measurement. Behind the shutter is positioned a UV responsive silicon photodetector (2207), such as but not limited to the S1336-8BQ silicon photodiode available form Hamamatsu (Hamamatsu City, Japan). In an alternative embodiment, UV diode source light is focused into a fiber optic assembly and transferred to ball lens (2203).

In various embodiments of the present invention, the radical dosimeter trans-illuminates the capillary and probes the same volume that is irradiated by the pump source. In this fashion, radical dosimetry can be performed on-line and after a single photolysis source flash, saving considerable time and sample when compared to the prior art. In some embodiments, the photolysis source optical train is arranged perpendicular, or off-axis, to the dosimeter optical train. In some embodiments, the dosimeter optical train shares components with the photolysis source optical train, so that light from the LED is launched into the photolysis source optical train in co-linear fashion. In the co-linear approach, LED light may be preferentially, but not exclusively, launched into the photolysis train by using a dichroic mirror, positioned at 45 degrees with respect to the photolysis train, that permits photolysis light to pass through and reflects LED dosimetry light into the optical train.

In some embodiments the radical dosimeter can be located down-stream of the photolysis cell, and as such, probes a distinct region of the fluidic circuit that does not receive photolysis light from a flash or laser source and or the like. In this case, shutter (2206) is not required, as the radical dosimeter photodetector (2207) does not receive photolysis light.

The described embodiments represent dosimeters compatible with FPOP experiments performed using $H_2O_2$ as a radical source. As known in the art, the background absorbance of $H_2O_2$ at 260 nm is minimal, thus enabling the measurement of adenine UV absorbance change at 260 nm without background interference. Radical dosimetry measurements made though the walls of a photolysis cell that is coated with metal oxide photo-catalyst is typically prohibited by excessive background absorbance. As shown in FIG. 13, $TiO_2$ and composite $TiO_2$ metal oxides exhibit significant UV absorbance at 260 nm, making it hard to measure changes in UV adenine absorbance. For metal oxide coated photolysis cells, radical dosimetry can be performed using a liquid core waveguide.

Figure 23:
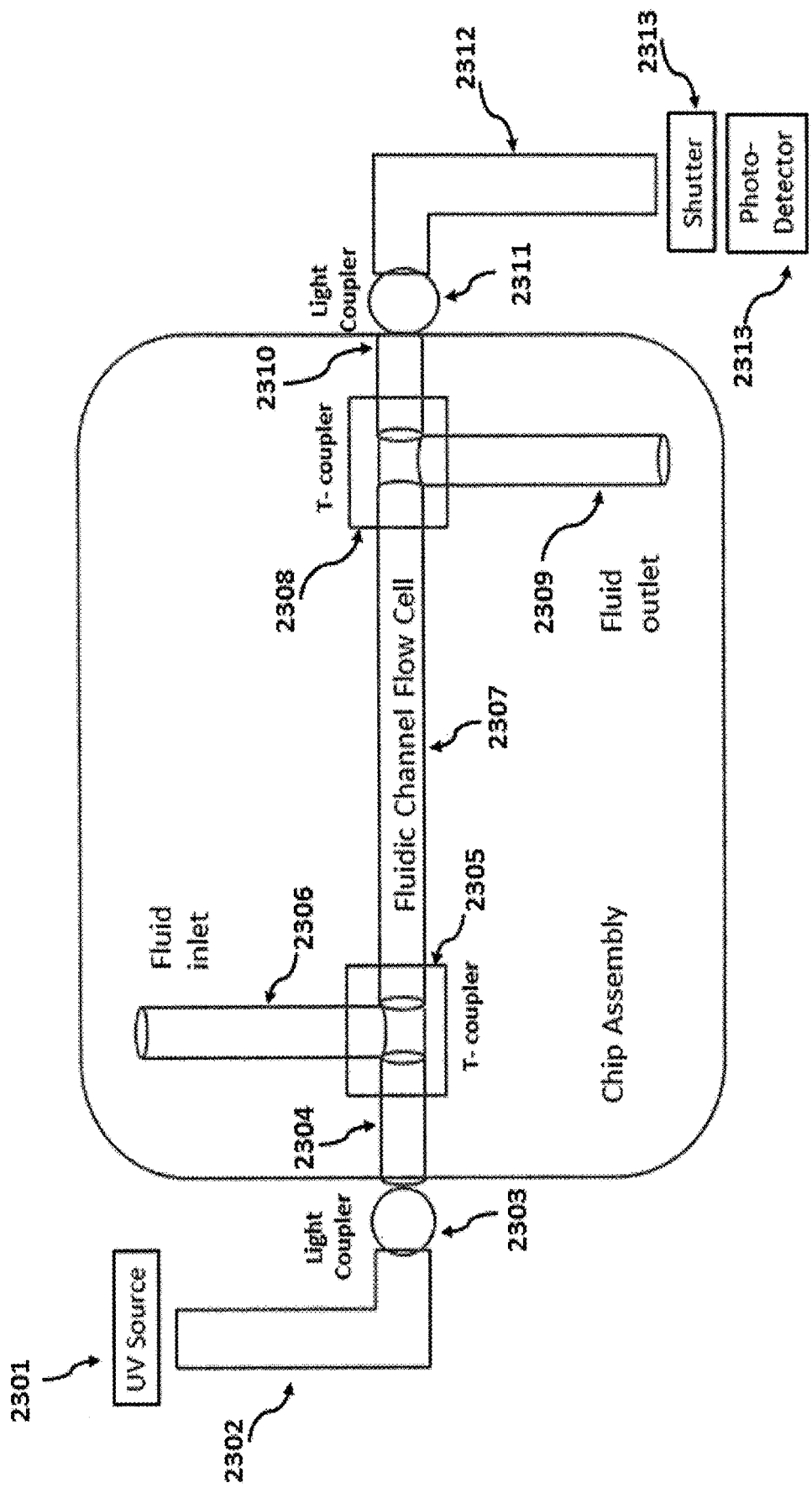
FIG. 23 depicts a liquid core waveguide dosimeter, according to various embodiments. Shown are: UV source (2301), input optical fiber (2302), optical coupler (2303), input optical fiber plug (2304), input opto-fluidic coupler (2305), fluid inlet line (2306), fluidic channel flow cell (2307), output opto-fluidic coupler (2308), fluid outlet line (2309), output optical fiber plug (2310), output optical coupler (2311), output optical fiber (2312), shutter assembly (2313) and photo detector (2314).

FIG. 23 depicts a liquid core waveguide dosimeter of the present invention. Dosimeter light is provided by a UV source (2301) which is launched into an input fiber (2302). Input fiber light is coupled into a fiber fluidic plug (2304) using a ball lens or comparable optical coupler (2303). Light exits the fiber plug (2304) and probes the sample fluid entering the inlet opto-fluidic coupler (2305) from a fluid inlet (2306). Dosimeter light is transmitted down the length of the photolysis flow cell (2307) by the process of total internal reflection. Sample fluid exits the photolysis cell via a fluid outlet (2309) after traveling through outlet opto-fluidic coupler (2308). Dosimeter light exits the photolysis cell by traveling through the outlet opto-fluidic coupler into an exit fiber plug (2310) and into an output fiber (2312) via an output coupler (2311). Light exits the output fiber and passes through a shutter assembly (2313) before impinging upon a photo detector (2314). In this fashion, UV absorbance of the dosimeter within the photolysis cell can be measured without the probe light passing through the high absorbing metal oxide. In some embodiments, the length of the fluidic channel is matched to closely approximate that of the pump source axial length striking the flow cell. In some embodiments, the photolysis cell is a capillary composed of appropriate material with outside and inside diameters as taught herein. In some embodiments, the photolysis cell is an opto-fluidic chip comprised of properties as further described herein.

In some embodiments using metal oxide photo-catalysts, radical dosimetry can be performed at a down-stream region of the microfluidic circuit that does not contain metal oxide photo-catalysts. In this manner, UV background absorption will be similar to that for $H_2O_2$ employed FPOP.

Figure 24:
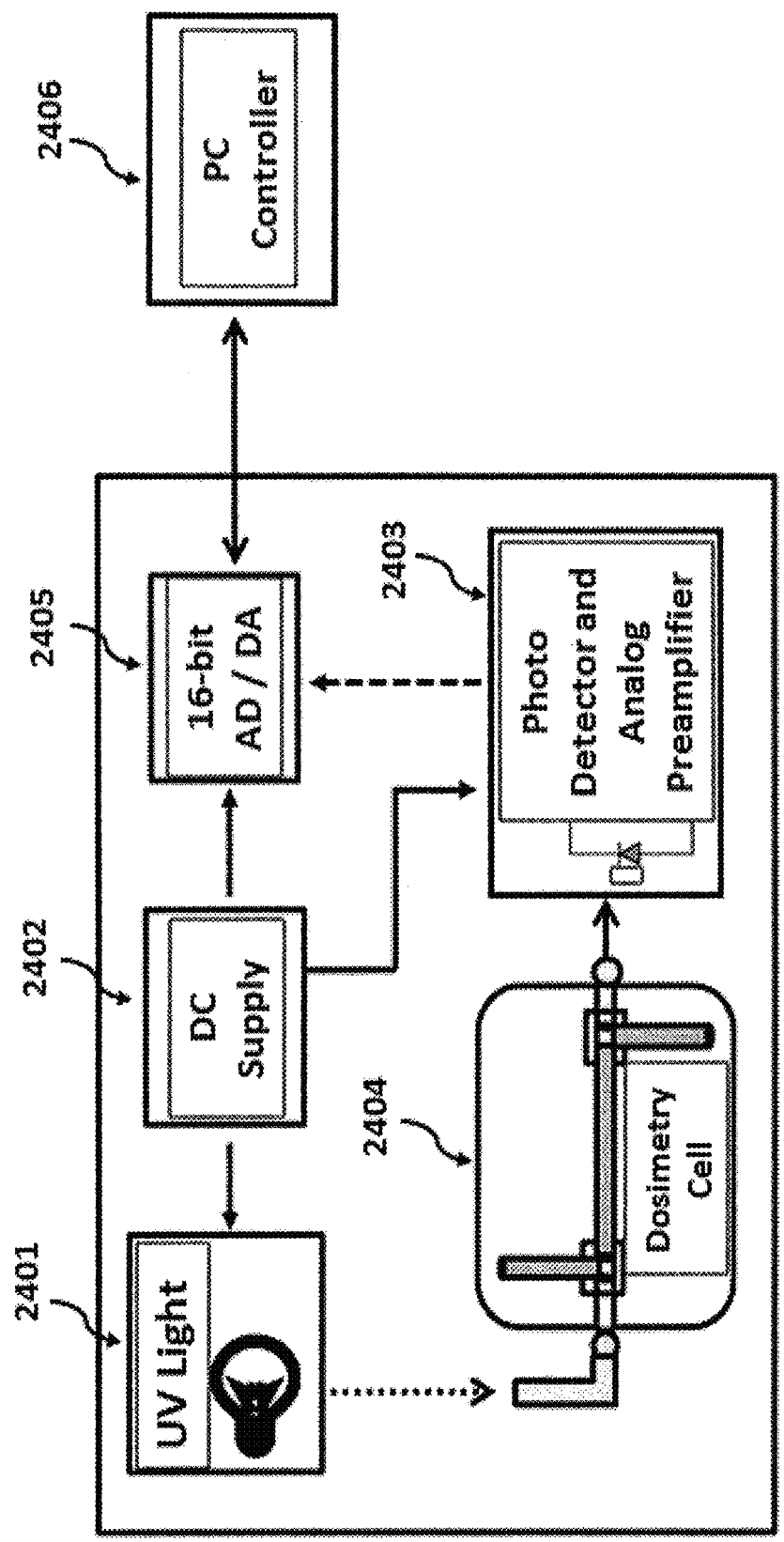
FIG. 24 depicts the radical dosimeter UV detector components, according to various embodiments. Illustrated are: UV light source (2401), DC power supply (2402), photo-detector circuitry and photo-diode assembly (2403), dosimetry cell (2404), ADC and DAC assembly (2405) and computer microprocessor (2406).

The radical dosimeter UV detector details are illustrated in FIG. 24. Power to the LED dosimeter light source (2401), which is an embodiment of (2301), is provided by a DC power supply (2402). The DC power supply further provides power to photodetector electronic assembly (2403) and analog-to-digital converter (ADC) (2405). Light from the LED source (2401) probes the dosimetry cell (2404) and impinges upon the photo-detector of photodetector electronic assembly. Within the photo-detector electronics assembly, photodiode output current is processed by a current to voltage (I to V) convertor, to provide a voltage that is proportional to photodiode incident light. Photodiode output voltage is transmitted to the ADC (2405) that creates a digital signal that is ultimately transmitted to the instrument controller (106) where UV absorbance calculations are performed.

Closed loop control to maintain consistent generation of effective OH radical load is optionally achieved by increasing or decreasing the drive voltage of the flash photolysis systems described herein in accordance with measured changes of adenine absorbance. Flash lamp drive voltage and subsequent spectral irradiance is increased to compensate for increased levels of background scavenging and concordantly decreased to adjust for diminished levels of scavenging. Compared to laser photonics, flash lamp system drive voltage can be adjusted with ease and precision across a broad dynamic range, without sacrificing pulse-to-pulse reproducibility. Irradiance can be varied between 0.1 and 20 $mJ/mm^2$-nm, with precision approaching 0.05 $mJ/mm^2$-nm. Because spectral irradiance is controlled using a common spot size, illumination volume remains constant, making for a simple system to model and employ for normalization. Because dosimetry is performed in the same optical region as photolysis, a single flash volume can be directly measured. As such, the present invention performs dosimetry without the need for multiple flash cycles or further transportation and manipulation of oxidized sample, saving considerable starting material and analysis time. As such, the flash lamp—closed loop control dosimetry approach is a simplified system to compensate for background scavenging of OH radicals, significantly enabling the practice of FPOP HRPF in a manner not demonstrated or taught in the prior art.

Calibrating the Closed-Loop Control Radical Dosimetry System

In a particular embodiment, the closed-loop control radical dosimetry system comprises a calibration function that is used to predict the required change in photolysis light source drive voltage in response to measured radical dosimeter photometric absorbance change. The calibration function is empirically determined through a plurality of measurements for which a known or control mixture of supporting buffer, analytical sample, and dosimeter internal standard are treated with a single flash of pump source light for each distinct control aliquot at a various drive voltage levels. In some embodiments, a software routine running in either the low-level instrument control or high level user interface programs, generates a look-up table that describes the measured change in dosimeter internal standard photometric absorbance at each drive voltage setting, allowing for the creation of a mathematical expression, or calibration function, that describes the relationship between applied drive voltage and measured dosimeter internal standard absorbance change for a single flash exposure. In some embodiments, the look-up table and subsequent calibration function is manually generated by the user employing absorbance change values for each photolysis source drive voltage value as reported by the present invention.

During sample processing, background hydroxyl radical scavenging is assessed via dosimetry. The measured change in dosimeter internal standard photometric absorbance is compared to a user specified targeted change. When the measured absorbance value deviates by $\geq +/-10\%$ from the target value, the photolysis light source drive voltage is altered to achieve the targeted change of measured absorbance. The calibration function is used to predict the required change in photolysis light source drive voltage.

Post-Analytical Normalization of Labeled Product Abundance

The disclosed approach alters spectral irradiance as a method of adjusting for unwanted changes in background scavenging of OH radicals, and as such represents a pre-analytical or pre-data processing scheme of correction. In some embodiments, it is also possible to apply scavenging correction to acquired HRPF data in a post-analytical or data processing manner. During post-analytical correction, the measured abundance of the oxidized species for an experimental trial, as detected by mass spectrometry or some other detection scheme such as but not limited to isoelectric focusing electrophoresis, is normalized by multiplying said response by a normalization factor derived from the ratio of dosimeter absorbance change determined between the experimental trial and reference trial. Specifically, the normalization factor is the ratio of the measured dosimeter absorbance change of the experimental trial divided by the measured dosimeter absorbance change of the reference trial. Alternatively, the normalization factor could comprise the ratio of the measured dosimeter absorbance change of the reference trial divided by the experimental trial. In this manner, for example, the ion current for a given protein mass spectrometry (MS) measurement or peptide single MS or tandem MS measurement could be adjusted by multiplying said ion current value by the determined normalization factor. For the purposes of disclosure, pre-analytical and post-analytical normalization schemes have been individually discussed. It should be recognized that the application of these two schemes are not mutually exclusive, and could be employed in tandem to achieve higher levels of compensation than achievable by exclusive application. In some embodiments, post-analytical normalization is applied to data acquired from HRPF experiments performed under the control of pre-analytical scavenging correction.

Flash Lamp Oxidation System Operational Cascade

For the various embodiments described herein, an operational method illustrates and exemplary order of unit operations that enables the device to function as an integrated and automated sample processing instrument. Exemplary operational methods are described for the purpose of elaborating the interplay of various sub-assemblies along with their ordered application. The illustrated methods are considered to be instructive and not limiting in scope, as other variants would be clear to those skilled in the art.

A protein sample of interest is pretreated by mixing with $H_2O_2$ and radical dosimeter internal standard, such as adenine. Samples are deposited upon the sample deck of the instrument. Referring back to FIG. 1, sample is aspirated from the sample vessel using the sample introduction system (101) and is transported into the photolysis cell. The radical dosimeter (104) measures the UV absorbance of the solution within the photolysis cell to establish the baseline (pre-photolysis) dosimeter internal standard absorbance. A single flash from the probe source is directed to strike the sample housed within the photolysis cell. Radical dosimetry is performed to assess the change in UV absorbance of dosimeter internal standard and the absorbance change is compared to target absorbance change to insure the appropriate level of target protein oxidation. If the change of absorbance exceeds the target value, then excessive levels of flash lamp irradiance was used. If the change of absorbance is less than the target value, then insufficient levels of flash lamp irradiance was used. Under control of the PC instrument controller (106) and system control electronics (105), the flash lamp power supply drive voltage (103) is altered by a software determined value predicted to be consistent with the difference between the measured and target change in dosimeter internal standard absorbance. A fresh sample aliquot is introduced into the photolysis cell by the sample introduction system. A backround dosimeter measurement is performed and a single probe source flash is applied, after which dosimeter absorbance measurement is assessed. The previously described cycle repeats until such time as target dosimeter absorbance change is achieved.

Once appropriate dosimetry values have been achieved, multiple sample aliquots are introduced and processed for a pre-determined number of cycles, producing a stream of product within the microfluidic circuit. Upon completion of the photolysis cycle, product is then deposited into the designated product reservoir by action of the sample collection system (101). The overarching cascade is repeated until the last sample in the sample introduction queue has been processed.

Biopharmaceutical Quality Control System Using Flash Lamp Oxidation

At various intervals during the manufacture of recombinantly expressed protein products, such as biopharmaceuticals, it is desirable to perform quality tests to insure that expressed product has been appropriately produced. Towards this end, it is desired to perform "by the kettle" analysis to establish that appropriate primary, secondary, tertiary, and quaternary structure has been maintained. HRPF represents a preferred means to evaluate and achieve desired product HOS. In some embodiments, a Biopharmaceutical Quality Control System comprises a flash oxidation system with closed-loop dosimeter, as described herein, hyphenated with isoelectric focusing (IEF) electrophoresis. Electrophoresis can be performed using either slab gel or capillary format. For hyphenation with slab-gel electrophoresis, collected product is introduced to the IEF device in an uncoupled and manual manner. For capillary IEF, sample introduction can proceed as it does with slab-gel, or samples could be automatically introduced via an on-line interface.

IEF analysis separates and detects the presence of proteins and peptides which differ by their isoelectric point (pI). As such, IEF represents an excellent means to detect variations in HOS for samples that have been treated by flash lamp oxidation, as solvent exposed amino acids will be selectively labeled with oxygen, thus shifting pI when compared to unlabeled starting material or to material of differing HOS. Since the flash lamp oxidation process is specific for a given biopharmaceutical tertiary and quaternary structure, differences in protein HOS among different product lots or between biosimilar and reference protein can be directly assessed by employing differential display analysis, as subsequently described herein. Differential analysis could be performed using intact protein or it could be performed using peptide populations for product protein digests. In addition to IEF, other separation/analysis means that detect variations in charge state distribution could be hyphenated with upstream flash lamp HRPF for by the kettle assessment of HOS. Examples of the latter include but are not limited to ion exchange liquid chromatography and hydrophilic interaction chromatography.

In a particular embodiment, a Biopharmaceutical Quality Control System comprises a flash oxidation system with closed-loop dosimeter, as described herein, hyphenated with fluorescence detection of carbonylated aliphatic amino acids as covalently labeled with a fluorescent dye such as, but not limited to, *Lucifer* Yellow; Alexa Flour 350, 405, 488, 555, 568, 594, and 633; and Cascade Blue C687 and or the like as sold by ThermoFisher Inc (San Jose, CA). Carbonylation of aliphatic side chains to form aldehyde or ketone moieties is one of the many reactions that occur in FPOP. As aliphatic amino acids are often buried in protein structure, the analytical value of discovering carbonylated aliphatic residues found on protein solvent addressable surface is especially useful for higher order structure comparative studies. When synthesized with either a hydrazide or cadaverine reactive group, the afore noted dyes specifically form covalent bonds with aldehyde and ketone functional groups of FPOP modified aliphatic amino acids. Since the flash lamp oxidation process is specific for a given biopharmaceutical tertiary and quaternary structure, differences in protein HOS among different product lots or between biosimilar and reference protein can be directly assessed by employing differential display analysis of measured fluorescence. In addition to carbonylation, HOS specific FPOP reactive products are also produced with sulfur containing amino acids such as methionine and cysteine. FPOP reactive moieties include, but are not limited to, sulfoxides, sulfones, sulfinic acid, and sulfonic acid. As with carbonylated FPOP products, sulfhydryl FPOP products can be specifically labeled by prudent selection of a variety specific reactive labeling fluorescence probes as known in the art.

Exemplary Sample Preparation and Analysis Protocols to Perform Flash HRPF

The following passages describe sample preparation and analysis protocols for the purpose of analyzing samples by flash HRPF, according to various embodiments. While illustrative, these protocols are not meant to be limiting in scope, as variants exist and would be evident to those skilled in the art.

Flash HRPF Using $H_2O_2$ and Adenine Radical Dosimeter

Analyte protein (~5 µM) is composed in solution with glutamine (17 mM), adenine (1 mM), and hydrogen peroxide (100 mM). Sample is introduced to the photolysis cell using flow rate of 10-100 microliters per minute. Flash photolysis and dosimetry is then performed. The UV absorbance of the dosimeter is fed-back into the flash lamp control system to deliver a consistent and reproducible effective concentration of hydroxyl radical to the solution as measured by a consistent loss of fractional absorbance at 260 nm (e.g. to maintain a 10% loss of absorbance), compensating for variances in flash lamp output, scavengers in solution, and changes in hydrogen peroxide concentration. Immediately after processing, the sample is deposited into a quenching solution consisting of a final concentration of 70 mM methionine amide and 1 µM catalase. The oxidized sample is later proteolytically digested and used for LC-MS(/MS) analysis of peptide and amino acid oxidation. Changes in protein topography will be determined based on changes in the amount of oxidation of affected amino acids compared to a reference protein footprint.

Liquid Chromatography-Photo-Oxidation System for HOS Characterization

Analyte protein of interest is applied to isocratic protein liquid chromatography (LC) (e.g. size exclusion chromatography). Immediately post-column, the eluent is split 10:1 with a make-up flow consisting of 1 M hydrogen peroxide, 10 mM adenine and 170 mM glutamine. The reconstituted eluent is introduced into the flash photolysis system using an in-line coupler as further described herein. Photolysis and dosimetry is performed as previously described. Immediately after processing, the sample is deposited into a product vessel, with each fraction deposited into a quenching solution consisting of a final concentration of 70 mM methionine amide and 1 µM catalase. The oxidized sample is then subsequently digested and used for LC-MS(/MS) analysis of peptide and amino acid oxidation. Changes in protein topography of each eluent present in a given fraction is determined based on changes in the amount of oxidation of affected amino acids compared to a reference protein footprint.

Isoelectric Focusing Analysis of HOS After Flash Lamp Oxidation

Analyte protein (~5 µM) is composed in solution with glutamine (17 mM), adenine (1 mM), and hydrogen peroxide (100 mM) in a 96-well format. Samples are processed as described above. Shortly after processing, samples are quenched by addition of a final concentration of 70 mM methionine amide and 1 µM catalase. Samples are removed from their product reservoir and applied to a pH 3-10 polyacrylamide isoelectric focusing protein gel. Samples will be separated by isoelectric point post-oxidation, and compared to a reference standard.

Additional Embodiments

Specific compositions and methods of a Flash Photo-Oxidation Device and Higher Order Structural Analysis have been disclosed. It should be apparent, however, to those skilled in the art that many more modifications besides those already described are possible without departing from the inventive concepts herein. The inventive subject matter, therefore, is not to be restricted except in the spirit of disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be presented or utilized, or combined with other elements, components, or steps that are not expressly referenced.

The general structure and techniques, and more specific embodiments which can be used to effect different ways of carrying out the more general goals are described herein. Although only a few embodiments have been disclosed in detail above, other embodiments are possible and the inventors intend these to be encompassed within this specification. The specification describes specific examples to accomplish a more general goal that may be accomplished in another way. This disclosure is intended to be exemplary, and the claims are intended to cover any modification or alternative that might be predictable to a person having ordinary skill in the art.

Also, the inventors intend that only those claims which use the words "means for" are intended to be interpreted under 35 USC 112, six paragraph. Moreover, no limitations from the specification are intended to be read into any claims, unless those limitations are expressly included in the claims. The computers described herein may be of any kind of computer, either general purpose, or some specific purpose computer such as a workstation or laboratory or manufacturing equipment. The computer may be an Intel (e.g., Pentium or Core 2 duo, i3 etc.) or AMD based computer, running Windows 10, 8, 7, or Linux, or may be a Macintosh computer. The computer may also be a hand-held computer such as a PDA, cellphone, tablet, or laptop, running any available operating system including Android, Windows Mobile, iOS, etc.

The programs may be written in C, C++, C#, Python, Java, Brew or any other programming language. The programs may be resident on a storage medium, e.g., magnetic or optical, e.g. the computer hard drive, a removable disk or media such as a memory stick or SD media, wired or wireless network based or Bluetooth based Network Attachment Storage (NAS), or other removable medium. The programs may also run over a network, for example, with a server or other machine sending signals to the local machine, which allows the local machine to carry out the operations described herein.

Various software components and/or embodiments of the present invention provide methods and/or systems for protein higher order structural analysis that can be implemented on a general purpose or special purpose information handling appliance, e.g., a computer, smart-phone, or information enabled laboratory, diagnostic, clinical, manufacturing, or consumer systems, using any suitable programming language such as Java, C++, C#, etc. and any suitable data or formatting specifications, such as HTML, XML, dHTML, TIFF, JPEG, tab-delimited text, binary, etc. Such software may be configured to perform the various steps disclosed herein and may be stored on a non-transient computer readable medium. In the interest of clarity, not all features of an actual implementation are described in this specification. It will be understood that in the development of any such actual implementation (as in any software development project), numerous implementation-specific decisions must be made to achieve the developers' specific goals and sub-goals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

All patents, and patent applications cited herein or filed with this application are incorporated by reference in their entirety.

Copyright Notice: Pursuant to 37 C.F.R. 1.71(e), applicant notes that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction.). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

What is claimed:

1. A method of selective labeling of solvent exposed molecular groups, the method comprising:
   introducing a sample mixture including a dosimeter internal standard into a photolysis cell of a flash photolysis system, wherein a change in dosimeter internal standard photometric absorbance represents an amount of produced free-radicals;
   determining a photometric absorbance of the sample mixture;
   irradiating the sample mixture with at least a first single pulse of photolysis light;
   determining a photometric absorbance change of the irradiated sample mixture and adjusting a spectral irradiance of the photolysis light source in response to the determined change in photometric absorbance; and
   analyzing products produced from the irradiated sample mixture, the analysis including detection of modified surface exposed functional groups.

2. The method of claim 1, wherein the sample mixture contains H2O2 as a OH radical photolysis source.

3. The method of claim 1, further comprising separating the introduced sample mixture into alternating regions of sample and gas partitions.

4. The method of claim 1, wherein the step of analyzing products is performed using mass spectrometry.

5. The method of claim 1, wherein the step of analyzing products is performed using iso-electric focusing.

6. The method of claim 1, wherein the step of analyzing products is performed using fluorescence detection of moiety specific reactive fluorescent dyes.

7. The method of claim 1, wherein the steps of determining the photometric absorbance and irradiating the sample mixture are both performed while the mixture is in the photolysis cell.

8. The method of claim 1, wherein the step of determining the photometric absorbance change is performed using a radical dosimeter, the radical dosimeter being configured for irradiating the products while the products are within the photolysis cell.

9. The method of claim 1, further comprising receiving the products produced in a product vessel, the photolysis cell, a radical dosimeter and the product vessel being in-line.

10. The method of claim 1, further comprising irradiating the sample mixture with at least a second single pulse of photolysis light, following the step of adjusting the spectral irradiance.

11. The method of claim 10, wherein the steps of irradiating the sample mixture with at least the first single pulse and of irradiating the sample mixture with at least the second single pulse are applied to different parts of the sample mixture in a micro-fluidic system.

12. The method of claim 1, further comprising separating the introduced sample mixture into alternating regions of sample and gas partitions, and further comprising irradiating the sample mixture with at least a second single pulse of photolysis light following the step of adjusting the spectral irradiance, wherein the steps of irradiating the sample mixture with at least the first single pulse and of irradiating the sample mixture with at least the second single pulse are applied to different sample partitions of the sample mixture.

13. The method of claim 12, wherein the step of separating the introduced sample into alternating regions is performed in a micro-fluidics system including the photolysis cell and a radical dosimeter.

14. A method of normalizing HRPF product abundance comprising:
  introducing a reference sample mixture into the photolysis cell of a flash photolysis system, the reference sample mixture including a dosimeter internal standard;
  determining the photometric absorbance of the reference sample mixture;
  irradiating the reference sample mixture using at least a single pulse of photolysis light;
  determining a change in photometric absorbance of said irradiated reference sample mixture, the change resulting from at least the single pulse;
  introducing an analyte sample mixture into the photolysis cell of the flash photolysis system, the analyte sample mixture including the dosimeter internal standard;
  determining the photometric absorbance of the analyte sample mixture;
  irradiating the analyte sample mixture using at least a single pulse of photolysis light;
  determining a photometric change in absorbance of the irradiated analyte sample mixture;
  analyzing a labeled reaction product produced from the irradiated analyte sample mixture; and
  multiplying a signal abundance of the labeled reaction product of the analyte sample mixture by a ratio of the change in photometric absorbance of the analyte sample mixture divided by the change in photometric absorbance of the reference sample mixture.

15. The method of claim 14, wherein the step of irradiating the analyte sample mixture is performed in a photolysis cell including $H_2O_2$ as a OH radical photolysis source.

16. The method of claim 14, further comprising receiving products produced in the step of irradiating the analyte sample in a product vessel, the product vessel being in-line with a photolysis cell and a radical dosimeter.

17. The method of claim 14, further comprising adjusting a spectral irradiance of the photolysis light used to irradiate the analyte sample mixture based on a dosimeter internal standard photometric absorbance measured in the analyte sample mixture, the dosimeter internal standard photometric absorbance being measured in-line with a photolysis cell in which the analyte sample mixture is irradiated.

18. The method of claim 14, further comprising adjusting a spectral irradiance of the photolysis light used to irradiate the analyte sample mixture based on a dosimeter internal standard photometric absorbance, the dosimeter internal standard photometric absorbance being measured in a microfluidics chip including a photolysis cell in which the analyte sample mixture is irradiated.

19. The method of claim 14, further comprising adjusting a spectral irradiance of the photolysis light used to irradiate the analyte sample mixture based on a dosimeter internal standard photometric absorbance, the dosimeter internal standard photometric absorbance being measured in-line with a photolysis cell in which the analyte sample mixture is irradiated and in-line with a product vessel configured to receive products of the irradiation of the sample mixture.

\* \* \* \* \*

UNITED STATES PATENT AND TRADEMARK OFFICE
CERTIFICATE OF CORRECTION

| | | |
|---|---|---|
| PATENT NO. | : 12,013,400 B2 | Page 1 of 1 |
| APPLICATION NO. | : 17/168472 | |
| DATED | : June 18, 2024 | |
| INVENTOR(S) | : Scot Randy Weinberger et al. | |

It is certified that error appears in the above-identified patent and that said Letters Patent is hereby corrected as shown below:

In the Specification

Column 1, Line 24, please insert the following header and paragraph before the "BACKGROUND" section therefor:
--STATEMENT OF GOVERNMENT SUPPORT
This invention was made with government support under grant number R43 GM137728 awarded by the National Institutes of Health. The government has certain rights in the invention.--

Signed and Sealed this
Fourth Day of March, 2025

Coke Morgan Stewart
*Acting Director of the United States Patent and Trademark Office*